(12) United States Patent
Tanaka et al.

(10) Patent No.: US 6,274,619 B1
(45) Date of Patent: Aug. 14, 2001

(54) AMIDINO SUBSTITUTED TETRAHYDROBENZO THIOPHENE OR FURAN DERIVATIVES AND THEIR USE AS UROKINASE INHIBITORS

(75) Inventors: Akito Tanaka, Takarazuka; Hiroaki Mizuno, Osaka; Minoru Sakurai, Toyonaka, all of (JP)

(73) Assignee: Fujisawa Pharmaceutical Co., Ltd., Osaka (JP)

(*) Notice: Subject to any disclaimer, the term of this patent is extended or adjusted under 35 U.S.C. 154(b) by 0 days.

(21) Appl. No.: 09/584,136

(22) Filed: May 31, 2000

Related U.S. Application Data

(63) Continuation of application No. 09/147,812, filed as application No. PCT/JP97/03215 on Sep. 12, 1997, now Pat. No. 6,093,710.

(30) Foreign Application Priority Data

Sep. 13, 1996 (AU) .................................. PO2278

(51) Int. Cl.$^7$ ..................... C07D 307/85; C07D 333/58; C07D 333/80; A61K 31/343; A61K 31/381
(52) U.S. Cl. ..................... 514/443; 514/468; 514/183; 514/211.1; 514/224.2; 549/49; 549/57; 549/467; 540/468; 540/552; 544/48
(58) Field of Search .................................. 514/443, 468; 549/49, 57, 467

(56) References Cited

U.S. PATENT DOCUMENTS

| | | | |
|---|---|---|---|
| 4,465,851 | 8/1984 | Muramatsu et al. | 560/125 |
| 5,089,634 | 2/1992 | Powers et al. | 549/285 |
| 5,093,332 | 3/1992 | Shepard et al. | 514/224.2 |
| 5,240,923 | 8/1993 | Dean et al. | 514/226.5 |
| 5,723,458 | 3/1998 | Brieaddy et al. | 514/211 |
| 5,889,002 | 3/1999 | Nielsen et al. | 514/222.8 |

FOREIGN PATENT DOCUMENTS

| | | |
|---|---|---|
| 568289 | 11/1993 | (EP) . |
| 618206 | 10/1994 | (EP) . |
| 2279951 | 1/1995 | (GB) . |

Primary Examiner—Mukund J. Shah
Assistant Examiner—Deepak R. Rao
(74) Attorney, Agent, or Firm—Oblon, Spivak, McClelland, Maier & Neustadt, P.C.

(57) ABSTRACT

A compound of the formula:

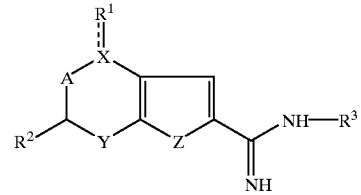

(I)

in which
$R^1$ is hydrogen, optionally substituted lower alkylcarbamoyl (lower)alkylidene, lower alkylidene, lower alkyl, optionally substituted ar(lower)alkyl, cyclo(lower)alkyl(lower) alkyl, protected carboxy(lower)alkyl, carboxy(lower) alkyl, hydroxy(lower)alkyl, optionally substituted lower alkylcarbamoyl(lower)alkyl, lower alkylthio(lower)alkyl, carboxy(lower)alkanoyl, protected carboxy(lower) alkanoyl, aroyl, lower alkanoyl, or optionally substituted arylcarbamoyl(lower)alkyl, $R^2$ is hydrogen, carboxy, protected carboxy, formyl or N-(lower)alkyl-N-(lower)alkoxycarbamoyl, $R^3$ is hydrogen or amidino-protective group, A is lower alkylene or carbonyl, X is

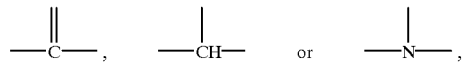

Y is lower alkylene, —S— or —SO$_2$—,
Z is —S— or —O—, and
the line: ═ is a single bond or a double bond, or pharmaceutically acceptable salts thereof,
which is useful as a medicament.

6 Claims, No Drawings

AMIDINO SUBSTITUTED TETRAHYDROBENZO THIOPHENE OR FURAN DERIVATIVES AND THEIR USE AS UROKINASE INHIBITORS

This application is a divisional of U.S. Ser. No. 09/147,812 file Mar. 12, 1999 now U.S. Pat. No. 6,093,710, which is a national stage application filed under 35 U.S.C. 371 of PCT/JP97/03215 filed Sep. 12, 1997.

TECHNICAL FILED

The present invention relates to novel compounds and pharmaceutically acceptable salts thereof.

More particularly, it relates to novel amidino derivatives and pharmaceutically acceptable salts thereof, which are useful as urokinase inhibitors, to processes for the preparation thereof, to a pharmaceutical composition comprising the same, to a use of the same as a medicament and to a method of the therapeutic treatment of diseases in a human being or an animal.

Accordingly, one object of the present invention is to provide novel amidino derivatives and pharmaceutically acceptable salts thereof, which are useful as urokinase inhibitors.

Another object of the present invention is to provide processes for the preparation of novel amidino derivatives and salts thereof.

A further object of the present invention is to provide a pharmaceutical composition comprising, as an active ingredient, said amidino derivatives and pharmaceutically acceptable salts thereof.

Urokinase (urokinase-type Plasminogen Activator, uPA) is a multi-domain serine protease which is able to convert the inactive precursor plasminogen to active plasmine.

Among the family of plasminogen activators, tissue type plasminogen activator (tPA) is present both in normal and in malignant tissue, whereas uPA has been shown to be produced abundantly by several common malignancies such as melanoma and colon, breast and prostate cancers.

Cellular invasiveness initiated by urokinase causes many physiological processes such as angiogenesis, neovascularization, bone restructuring, embryo implantaion in the uterus (embryonic development), infiltration of immune cells into inflammatory sites, ovulation, trophoblast implantation, breast, uterine, and prostatic involution, spermatogenesis, tissue remodeling during wound repair (wound healing) and organ differentiation, fibrosis, local invasion of tumors into adjacent areas (tumor invasion), metastatic spread of tumor cells from primary to secondary sites (tumor metastasis), and tissue destruction in arthritis.

Inhibitors of urokinase therefore have mechanism-based anti-angiogenic, anti-arthritic, anti-inflammatory, anti-invasive, anti-metastatic, anti-osteoporotic, anti-retinopathic (for angiogenesis-dependent retinopathies), contraceptive, and tumoristatic activities.

DISCLOSURE OF INVENTION

The object amidino derivatives are novel and can be represented by the following general formula:

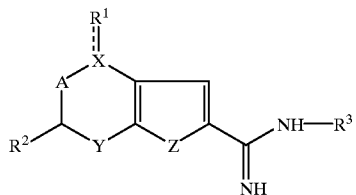

(I)

in which $R^1$ is hydrogen, optionally substituted lower alkylcarbamoyl (lower)alkylidene, lower alkylidene, lower alkyl, optionally substituted ar(lower)alkyl, cyclo(lower)alkyl(lower)alkyl, protected carboxy(lower)alkyl, carboxy(lower)alkyl, hydroxy(lower)alkyl, optionally substituted lower alkylcarbamoyl(lower)alkyl, lower alkylthio(lower)alkyl, carboxy(lower)alkanoyl, protected carboxy(lower)alkanoyl, aroyl, lower alkanoyl, or optionally substituted arylcarbamoyl(lower)alkyl, $R^2$ is hydrogen, carboxy, protected carboxy, formyl or N-(lower) alkyl-N-(lower) alkoxycarbamoyl, $R^3$ is hydrogen or amidino-protective group, A is lower alkylene or carbonyl, X is

Y is lower alkylene, —S— or —SO$_2$—,

Z is —S— or —O—, and the line: ═ is a single bond or double bond, or pharmaceutically acceptable salts thereof.

Suitable salts of the object compound (I) are pharmaceutically acceptable, conventional non-toxic salts and may include;

a salt with a base such as an inorganic base salt, for example, an alkali metal salt (e.g. sodium salt, potassium salt, etc.), an alkaline earth metal salt (e.g. calcium salt, magnesium salt, etc.), an ammonium salt, an organic base salt, for example, an organic amine salt (e.g. triethylamine salt, pyridine salt, picoline salt, ethanolamine salt, triethanolamine salt, dicyclohexylamine salt, N,N'-dibenzylethylenediamine salt, etc.);

a salt with an acid such as inorganic acid addition salt (e.g. hydrochloride, hydrobromide, sulfate, phosphate, etc.), an organic acid addition salt (e.g. formate, acetate, trifluoroacetate, maleate, tartrate, fumarate, methanesulfonate, benzenesulfonate, etc.);

a salt with a basic or acidic amino acid (e.g. arginine, aspartic acid, glutamic acid, etc.); and the like.

The object compound (I) and pharmaceutically acceptable salt thereof may include a solvate [e.g. enclosure compound (e.g., hydrate, etc.)].

It is to be noted that the compound (I) and the other compounds may include one or more stereoisomers due to asymmetric carbon atoms, and all of such isomers and mixture thereof are included within the scope of this invention.

According to the present invention, the object compound (I) or pharmaceutically acceptable salts thereof can be prepared by the processes as illustrated by the following reaction schemes.

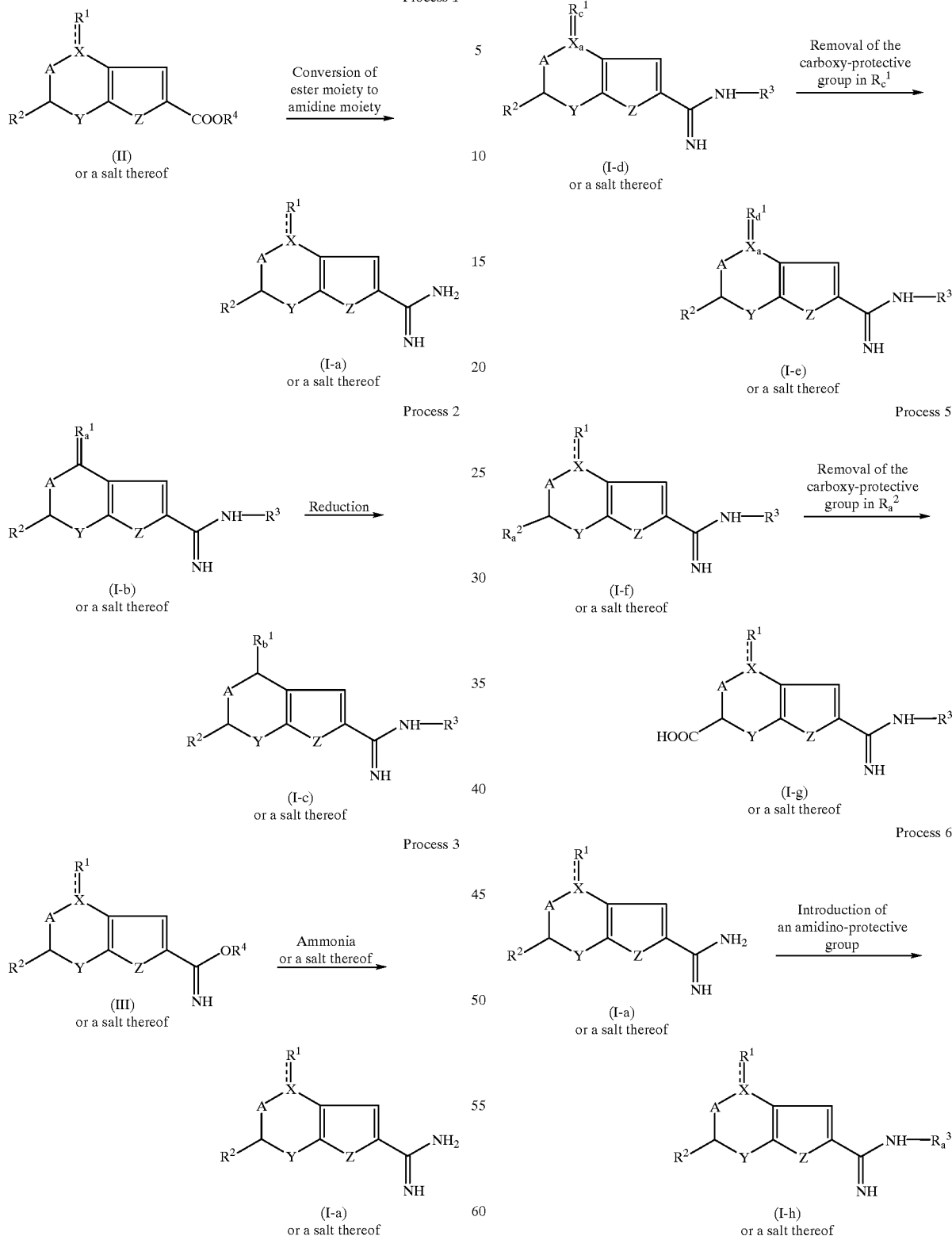

Process 7

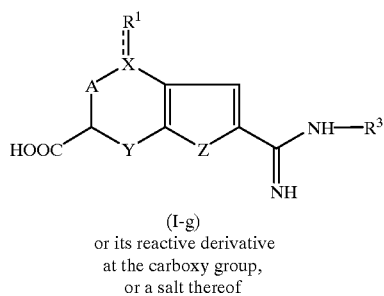

(I-g) or its reactive derivative at the carboxy group, or a salt thereof

→ N- (lower) alkyl-N- (lower) alkoxy-amine or a salt thereof

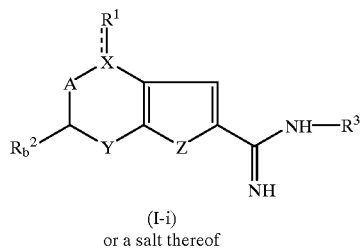

(I-i) or a salt thereof

Process 8

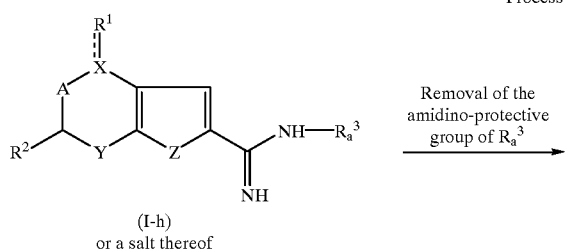

(I-h) or a salt thereof

→ Removal of the amidino-protective group of $R_a^3$

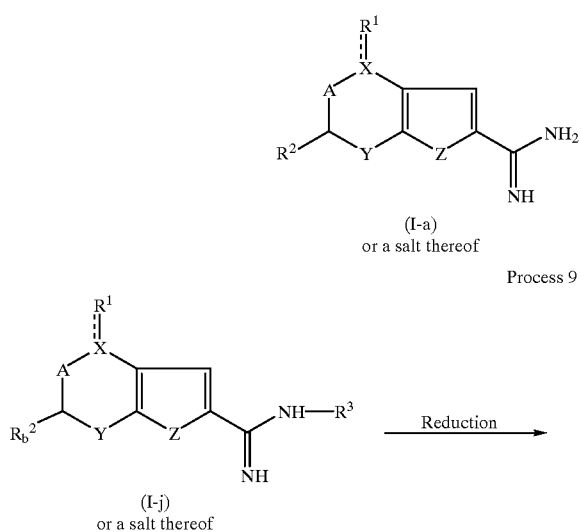

(I-a) or a salt thereof

Process 9

(I-j) or a salt thereof

→ Reduction

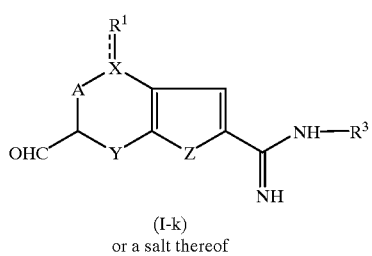

(I-k) or a salt thereof in which
$R^1, R^2, R^3, A, X, Y, Z$ and the line: ═ are each as defined above,
$R_a^1$ is optionally substituted lower alkylcarbamoyl(lower)alkylidene or lower alkylidene,
$R_b^1$ is optionally substituted lower alkylcarbamoyl(lower)alkyl or lower alkyl,
$R_c^1$ is protected carboxy(lower)alkyl or protected carboxy(lower)alkanoyl,
$R_d^1$ is carboxy(lower)alkyl or carboxy(lower)alkanoyl,
$R_a^2$ is protected carboxy,
$R_b^2$ is N-(lower)alkyl-N-(lower)alkoxycarbamoyl,
$R_a^3$ is amidino-protective group,
$R^4$ is ester residue,
$X_a$ is

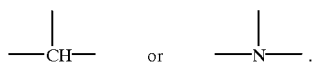

The object compounds thus obtained can be converted to its salt by a conventional method.

The compound (II) used in the Process 1 may be new and can be prepared, for example, according to the following Preparations or by a conventional manner.

In the descriptions of the present specification, suitable examples and illustrations of the various definitions which the present invention includes within the scope thereof are explained in detail as follows.

The term "lower" is intended to mean 1 to 6 carbon atom(s), preferably 1 to 4 carbon atom(s), unless otherwise indicated.

Suitable "lower alkoxy" may include straight or branched one such as methoxy, ethoxy, propoxy, isopropoxy, butoxy, t-butoxy, pentyloxy, hexyloxy, and the like, and the most preferable example may be methoxy.

Suitable "lower alkyl" may include straight or branched one such as methyl, ethyl, propyl, isopropyl, butyl, t-butyl, pentyl, hexyl, and the like, and the most preferable example may be ethyl and butyl for $R^1$.

Suitable "ester residue" means a group substituted with the hydrogen atom in the "esterified carboxy" as mentioned below.

Suitable "optionally substituted arylcarbamoyl(lower)alkyl" means aforementioned lower alkyl substituted by arylcarbamoyl group such as phenylcarbamoyl, tolylcarbamoyl, xylylcarbamoyl, cumenylcarbamoyl, mesitylcarbamoyl, naphthylcarbamoyl, and the like, and said arylcarbamoyl group is optionally substituted by the group consisting of lower alkyl as mentioned above, lower alkoxy as mentioned above, and lower alkylenedioxy as mentioned below, in which more preferable example may be phenylcarbamoyl(lower)alkyl optionally substituted by lower alkylenedioxy, and the most preferable one may be 3,4-methylenedioxyphenylcarbamoylmethyl.

Suitable "halogen" may include fluorine, bromine, chlorine and iodine, in which more preferable example may be fluorine.

Suitable "cyclo(lower)alkyl(lower)alkyl" means aforementioned lower alkyl substituted by cyclo(lower)alkyl as mentioned below, in which the most preferable example may be cyclohexylmethyl.

Suitable "optionally substituted ar(lower)alkyl" means aforementioned lower alkyl substituted by aryl as mentioned below, in which said aryl group is optionally substituted by the group consisting of lower alkyl as mentioned above, lower alkoxy as mentioned above, and lower alkylenedioxy as mentioned below, wherein more preferable example may be $C_6$–$C_{10}$ ar(lower)alkyl optionally substituted by one or two suitable substituents selected from the group consisting of lower alkoxy and lower alkylenedioxy, and the most preferable one may be benzyl, phenethyl, 3,4-dimethoxyphenethyl and 3,4-methylenedioxyphenethyl.

Suitable "lower alkylenedioxy" may include straight or branched one such as methylenedioxy, ethylenedioxy, trimethylenedioxy, tetramethylenedioxy, pentamethylenedioxy, hexamethylenedioxy, methylmethylenedioxy, ethylethylenedioxy, propylenedioxy, and the like, in which the most preferable one may be methylenedioxy.

Suitable "cyclo(lower)alkyl" may include cyclo($C_3$–$C_6$)-alkyl such as cyclopropyl, cyclobutyl, cyclopentyl, cyclohexyl, and the like, in which the most preferable example may be cyclohexyl.

Preferable "aryl" may include $C_6$–$C_{10}$ aryl such as phenyl, tolyl, xylyl, cumenyl, mesityl, naphthyl, etc., in which the most preferable one may be phenyl.

Suitable "lower alkylidene" may include straight or branched one such as methylene, ethylidene, propylidene, isopropylidene, butylidene, pentylidene, hexylidene, methylmethylidene, ethylethylidene, propylidene, and the like, in which the most preferred one may be butylidene for $R^1$.

Suitable "optionally substituted lower alkylcarbamoyl (lower)alkylidene" means aforementioned lower alkylidene substituted by optionally substituted lower alkylcarbamoyl as mentioned below, wherein the most preferable example may be n-butylcarbamoylmethylidene.

Suitable "optionally substituted lower alkylcarbamoyl (lower)alkyl" means aforementioned lower alkyl substituted by "optionally substituted lower alkylcarbamoyl" as mentioned below, wherein the most preferable example may be n-butylcarbamoylmethyl and 2,2,2-trifluoroethylcarbamoylmethyl.

Suitable "optionally substituted lower alkylcarbamoyl" may include carbamoyl substituted by aforementioned lower alkyl, in which the lower alkyl group is optionally substituted by halogen as mentioned above, the most preferable one may be n-butylcarbamoyl and 2,2,2-trifluoroethylcarbamoyl.

Suitable "hydroxy(lower)alkyl" may include straight or branched one such as hydroxymethyl, hydroxyethyl, hydroxypropyl, hydroxybutyl, hydroxypentyl, hydroxyhexyl, and the like, in which the most preferable one may be 2-hydroxyethyl.

Suitable "lower alkylene" may include straight or branched one such as methylene, ethylene, trimethylene, tetramethylene, pentamethylene, hexamethylene, methylmethylene, ethylethylene, propylene, and the like, in which the most preferable one may be methylene for A and Y, and ethylene for Y.

Suitable "protected carboxy" may include esterified carboxy as mentioned below.

"Esterified carboxy" can be referred to the ones as mentioned below.

Suitable examples of the ester moiety of an esterified carboxy may be the ones such as lower alkyl ester (e.g. methyl ester, ethyl ester, propyl ester, isopropyl ester, butyl ester, isobutyl ester, t-butyl ester, pentyl ester, hexyl ester, etc.) which may have at least one suitable substituent(s) for example, lower alkanoyloxy(lower)alkyl ester [e.g. acetoxymethyl ester, propionyloxymethyl ester, butyryloxymethyl ester, valeryloxymethyl ester, pivaloyloxymethyl ester, hexanoyloxymethyl ester, 1-(or 2-)acetoxyethyl ester, 1-(or 2- or 3-)acetoxypropyl ester, 1-(or 2- or 3- or 4-)acetoxybutyl ester, 1-(or 2-)propionyloxyethyl ester, 1-(or 2- or 3-)propionyloxypropyl ester, 1-(or 2-)butyryloxyethyl ester, 1-(or 2-)isobutyryloxyethyl ester, 1-(or 2-)pivaloyloxyethyl ester, 1-(or 2-)hexanoyloxyethyl ester, isobutyryloxymethyl ester, 2-ethylbutyryloxymethyl ester, 3,3-dimethylbutyryloxymethyl ester, 1-(or 2-)pentanoyloxyethyl ester, etc.], aroyl(lower)alkyl ester such as benzoyl(lower)alkyl ester (e.g. phenacyl ester, etc.), lower alkanesulfonyl(lower)alkyl ester (e.g. 2-mesylethyl ester, etc.), mono(or di or tri)halo(lower)alkyl ester (e.g. 2-iodoethyl ester, 2,2,2-trichloroethyl ester, etc.); lower alkoxycarbonyloxy(lower)alkyl ester [e.g. methoxycarbonyloxymethyl ester, ethoxycarbonyloxymethyl ester, propoxycarbonyloxymethyl ester, t-butoxycarbonyloxymethyl ester, 1-(or 2-)methoxycarbonyloxyethyl ester, 1-(or 2-)ethoxycarbonyloxyethyl ester, 1-(or 2-)isopropoxycarbonyloxyethyl ester, etc.], phthalidylidene (lower)alkyl ester, or (5-lower alkyl-2-oxo-1,3-dioxol-4-yl) (lower)alkyl ester [e.g. (5-methyl-2-oxo-1,3-dioxol-4-yl) methyl ester, (5-ethyl-2-oxo-1,3-dioxol-4-yl)methyl ester, (5-propyl-2-oxo-1,3-dioxol-4-yl)ethyl ester, etc.]; lower alkenyl ester (e.g. vinyl ester, allyl ester, etc.); lower alkynyl ester (e.g. ethynyl ester, propynyl ester, etc.); ar(lower)alkyl ester which may have at least one suitable substituent(s) (e.g. benzyl ester, 4-methoxybenzyl ester, 4-nitrobenzyl ester, phenethyl ester, trityl ester, benzhydryl ester, bis (methoxyphenyl)methyl ester, 3,4-dimethoxybenzyl ester, 4-hydroxy-3,5-di-t-butylbenzyl ester, etc.); aryl ester which may have at least one suitable substituent(s) (e.g. phenyl ester, 4-chlorophenyl ester, tolyl ester, t-butylphenyl ester, xylyl ester, mesityl ester, cumenyl ester, etc.); phthalidyl ester; and the like.

Preferable examples of the protected carboxy thus defined may be lower alkoxycarbonyl.

Suitable "carboxy(lower)alkyl" means aforementioned lower alkyl which is substituted by carboxy, wherein the preferable examples may be carboxymethyl.

Suitable "protected carboxy(lower)alkyl" means aforementioned lower alkyl which is substituted by abovementioned "protected carboxy", wherein more preferable example may be lower alkoxycarbonyl(lower)alkyl, phenyl (lower)alkoxycarbonyl(lower)alkyl and benzoyl(lower) alkoxycarbonyl(lower)alkyl, and the most preferable one may be ethoxycarbonylmethyl and ethoxycarbonylpropyl.

Suitable "N-(lower)alkyl-N-(lower)alkoxycarbamoyl" means carbamoyl group N-substituted by lower alkyl as mentioned above and also N-substituted by lower alkoxy as mentioned above, in which more preferable example may be N-($C_1$–$C_4$)-alkyl-N-($C_1$–$C_4$)alkoxycarbamoyl, and the most preferable one may be N-methyl-N-methoxycarbamoyl.

Suitable "amidino-protective group may include acyl.

Suitable "acyl" may include carbamoyl, aliphatic acyl group and acyl group containing an aromatic ring, which is referred to as aromatic acyl, or heterocyclic ring, which is referred to as heterocyclic acyl.

Suitable example of said acyl may be illustrated as follows:

Carbamoyl; Thiocarbamoyl; Sulfamoyl;

Aliphatic acyl such as lower or higher alkanoyl (e.g., formyl, acetyl, propanoyl, butanoyl, 2-methylpropanoyl, pentanoyl, 2,2-dimethylpropanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl, icosanoyl, etc.); lower or higher alkoxycarbonyl (e.g., methoxycarbonyl, ethoxycarbonyl, t-butoxycarbonyl, t-pentyloxycarbonyl, heptyloxycarbonyl, etc.);

lower or higher alkylsulfonyl (e.g., methylsulfonyl, ethylsulfonyl, etc.);

lower or higher alkoxysulfonyl (e.g., methoxysulfonyl, ethoxysulfonyl, etc.);

mono(or di or tri)halo(lower)alkylsulfonyl [e.g. fluoromethylsulfonyl, dichloromethylsulfonyl, trifluoromethylsulfonyl, chloromethylsulfonyl, dichloromethylsulfonyl, trichloromethylsulfonyl, 1 or 2-fluoroethylsulfonyl, 1 or 2-chloroethylsulfonyl, etc.);

or the like;

Aromatic acyl such as aroyl (e.g., benzyl, toluoyl, naphthoyl, etc.);

ar(lower)alkanoyl [e.g., phenyl(lower)alkanoyl (e.g., phenylacetyl, phenylpropanoyl, phenylbutanoyl, phenylisobutanoyl, phenylpentanoyl, phenylhexanoyl, etc.), naphthyl(lower)alkanoyl (e.g., naphthylacetyl, naphthylpropanoyl, naphthylbutanoyl, etc.), etc.];

ar(lower)alkenoyl [e.g., phenyl(lower)alkenoyl (e.g., phenylpropenoyl, phenylbutenoyl, phenylmethacryloyl, phenylpentenoyl, phenylhexenoyl, etc.), naphthyl(lower) alkenoyl (e.g., naphthylpropenoyl, naphthylbutenoyl, etc.), etc.];

ar(lower)alkoxycarbonyl [e.g., phenyl(lower) alkoxycarbonyl (e.g., benzyloxycarbonyl, etc.), etc.];

aryloxycarbonyl (e.g., phenoxycarbonyl, naphthyloxycarbonyl, etc.);

aryloxy(lower)alkanoyl (e.g., phenoxyacetyl, phenoxypropionyl, etc.);

arylglyoxyloyl (e.g., phenylglyoxyloyl, naphthylglyoxyloyl, etc.);

arylsulfonyl (e.g., phenylsulfonyl, p-tolylsulfonyl, etc.);

or the like;

Heterocyclic acyl such as heterocycliccarbonyl;

heterocyclic(lower)alkanoyl (e.g., heterocyclicacetyl, heterocyclicpropanoyl, heterocyclicbutanoyl, heterocyclicpentanoyl, heterocyclichexanoyl, etc.);

heterocyclic(lower)alkenoyl (e.g., heterocyclicpropenoyl, heterocyclicbutenoyl, heterocyclicpentenoyl, heterocyclichexenoyl, etc.);

heterocyclicglyoxyloyl; or the like.

in which suitable "heterocyclic moiety" in the terms "heterocycliccarbonyl", "heterocyclic(lower)alkyl", heterocyclic(lower)alkenoyl" and "heterocyclicglyoxyloyl" as mentioned above means, in more detail, saturated or unsaturated, monocyclic or polycyclic heterocyclic group containing at least one hetero-atom such as an oxygen, sulfur, nitrogen atom and the like.

And, especially preferable heterocyclic group may be heterocyclic group such as unsaturated 3 to 8-membered (more preferably 5 or 6-membered) heteromonocyclic group containing 1 to 4 nitrogen atom(s), for example, pyrrolyl, pyrrolinyl, imidazolyl, pyrazolyl, pyridyl, dihydropyridyl, pyrimidinyl, pyrazinyl, pyridazinyl, triazolyl (e.g., 4H-1,2,4-triazolyl, 1H-1,2,3-triazolyl, 2H-1,2,3-triazolyl, etc.), tetrazolyl (e.g., 1H-tetrazolyl, 2H-tetrazolyl, etc.), etc.;

saturated 3 to 8-membered (more preferably 5 or 6-membered) heteromonocyclic group containing 1 to 4 nitrogen atom(s), for example, pyrrolidinyl, imidazolidinyl, piperidyl, piperazinyl, etc.;

unsaturated condensed heterocyclic group containing 1 to 4 nitrogen atom(s), for example, indolyl, isoindolyl, indolinyl, indolizinyl, benzimidazolyl, quinolyl, isoquinolyl, indazolyl, benzotriazolyl, etc.;

unsaturated 3 to 8-membered (more preferably 5 or 6-membered) heteromonocyclic group containing 1 to 2 oxygen atom(s) and 1 to 3 nitrogen atom(s), for example, oxazolyl, isoxazolyl, oxadiazolyl (e.g., 1,2,4-oxadiazolyl, 1,3,4-oxadiazolyl, 1,2,5-oxadiazolyl, etc.), etc.;

saturated 3 to 8-membered (more preferably 5 or 6-membered) heteromonocyclic group containing 1 to 2 oxygen atom(s) and 1 to 3 nitrogen atom(s), for example, oxazolidinyl, morpholinyl, sydnonyl, etc.;

unsaturated condensed heterocyclic group containing 1 to 2 oxygen atom(s) and 1 to 3 nitrogen atom(s), for example, benzoxazolyl, benzoxadiazolyl, etc.;

unsaturated 3 to 8-membered (more preferably 5 or 6-membered) heteromonocyclic group containing 1 to 2 sulfur atom(s) and 1 to 3 nitrogen atom(s), for example, triazolyl, isothiazolyl, thiadiazolyl (e.g., 1,2,3-thiadiazolyl, 1,2,4-thiadiazolyl, 1,3,4-thiadiazolyl, 1,2,5-thiadiazolyl, etc.), dihydrothiazinyl, etc.;

saturated 3 to 8-membered (more preferably 5 or 6-membered) heteromonocyclic group containing 1 to 2 sulfur atom(s) and 1 to 3 nitrogen atom(s), for example, thiazolidinyl, etc.;

unsaturated 3 to 8-membered (more preferably 5 or 6-membered) heteromonocyclic group containing 1 to 2 sulfur atom(s) for example, thienyl, dihydrodithiinyl, dihydrodithionyl, etc.;

unsaturated condensed heterocyclic group containing 1 to 2 sulfur atom(s) and 1 to 3 nitrogen atom(s), for example, benzothiazolyl, benzothiadiazolyl, etc.;

unsaturated 3 to 8-membered (more preferably 5 or 6-membered) heteromonocyclic group containing an oxygen atom, for example, furyl, etc.;

unsaturated 3 to 8-membered (more preferably 5 or 6-membered) heteromonocyclic group containing an oxygen atom and 1 to 2 sulfur atom(s), for example, dihydrooxathiinyl, etc.;

unsaturated condensed heterocyclic group containing 1 to 2 sulfur atom(s), for example, benzothienyl, benzodithiinyl, etc.;

unsaturated condensed heterocyclic group containing an oxygen atom and 1 to 2 sulfur atom(s), for example, benzoxathiinyl, etc.; and the like.

The acyl moiety as stated above may have one to ten, same or different, suitable substituent(s) such as lower alkyl as exemplified above; lower alkoxy as exemplified above; lower alkylthio wherein lower alkyl moieties as exemplified above; lower alkylamino wherein lower alkyl moiety is as exemplified above; cyclo(lower)alkyl as exemplified above; cyclo(lower)alkenyl as exemplified above; halogen; amino, protected amino as exemplified above; hydroxy; protected hydroxy; cyano; nitro; carboxy; protected carboxy; sulfo; sulfamoyl; imino; oxo; amino(lower)alkyl wherein lower alkyl moiety is as exemplified above; carbamoyloxy; hydroxy(lower)alkyl wherein lower alkyl moiety is as exemplified above; diamino(lower)alkylidene (e.g., diaminomethylene, etc.); di(lower)alkylamino wherein lower alkyl moiety is as exemplified above; di(lower) alkylamino(lower)alkyl wherein lower alkyl moiety is as exemplified above; heterocyclic(lower)alkyl wherein heterocyclic moiety and lower alkyl moiety are each as exemplified above, or the like.

Preferable example of amidino-protective group thus defined may be lower alkoxycarbonyl, and the most preferable one may be t-butoxycarbonyl.

Suitable "lower alkanoyl" may include formyl, acetyl, propanoyl, butanoyl, 2-methylpropanoyl, pentanoyl, 2,2-dimethylpropanoyl, hexanoyl, and the like, in which more preferable example may be $C_1$–$C_4$ alkanoyl and the most preferable one may be acetyl.

Suitable "carboxy(lower)alkanoyl" means lower alkanoyl as mentioned above substituted by carboxy, in which more preferable example may be carboxy($C_1$–$C_4$)alkanoyl and the most preferable one may be carboxyacetyl.

Suitable "protected carboxy(lower)alkanoyl" means lower alkanoyl as mentioned above substituted by protected carboxy as mentioned above, in which more preferable example may be $C_1$–$C_4$ alkoxycarbonyl($C_1$–$C_4$)alkanoyl and the most preferable one may be ethoxycarbonylacetyl.

Suitable "aroyl" may include $C_6$–$C_{10}$ aroyl such as benzoyl, toluoyl, naphthoyl, and the like, in which the most preferable one may be benzoyl.

One preferable embodiments of $R^1$, $R^2$, $R^3$, A, X, Y, Z and the line: ══ are as follows:

$R^1$ is hydrogen, lower alkylcarbamoyl(lower)alkylidene optionally substituted by halogen, lower alkylidene, lower alkyl, ar(lower)alkyl optionally substituted by the group consisting of lower alkyl, lower alkoxy and lower alkylenedioxy, cyclo(lower)alkyl(lower)alkyl, lower alkoxycarbonyl(lower)alkyl, carboxy(lower)alkyl, hydroxy(lower)alkyl, lower alkylcarbamoyl(lower)alkyl optionally substituted by halogen, or arylcarbamoyl(lower)alkyl optionally substituted by the group consisting of lower alkyl, lower alkoxy and lower alkylenedioxy, $R^2$ is hydrogen,
$R^3$ is hydrogen,
A is lower alkylene or carbonyl,
X is

Y is lower alkylene, —S— or —$SO_2$—,
Z is —S— or —O—, and
the line: ══ is single bond or double bond.

The processes for the preparation of the object compound (I) of the present invention are explained in detail in the following.

(1) Process 1

The compound (I-a) or a salt thereof can be prepared by converting the ester moiety of the compound (II) or a salt thereof to the amidino moiety.

Suitable salts of the compounds (I-a) and (II) may be the same as those for the compound (I).

This reaction can be carried out by a conventional method which can convert the ester moiety to the amidine moiety such as reacting with a combination of ammonium halide (e.g. ammonium chloride, etc.) and tri(lower)alkylalminum (e.g. trimethylalminum, etc.).

This reaction can be carried out in a conventional solvent which does not adversely influence the reaction such as dichloromethane, pyridine, N,N-dimethylformamide, 4-methyl-2-pentanone, tetrahydrofuran, toluene, etc., or a mixture thereof.

The reaction temperature is not critical and the reaction is usually carried out under from warming to heating.

(2) Process 2

The compound (I-c) or a salt thereof can be prepared by reducing the compound (I-b) or a salt thereof.

Suitable salts of the compounds (I-b) and (I-c) may be the same as those for the compound (I)

The reduction method applicable for this removal reaction may include, for example, reduction by using a combination of a metal (e.g. zinc, zinc amalgam, etc.) or a salt of chrome compound (e.g. chromous chloride, chromous acetate, etc.) and an organic or inorganic acid (e.g. acetic acid, propionic acid, hydrochloric acid, sulfuric acid, etc.); and conventional catalytic reduction in the presence of a conventional metallic catalyst such as palladium catalysts (e.g. spongy palladium, palladium black, palladium oxide, palladium on carbon, colloidal palladium, palladium on barium sulfate, palladium on barium carbonate, palladium hydroxide on carbon, etc.), nickel catalysts (e.g. reduced nickel, nickel oxide, Raney nickel, etc.), platinum catalysts (e.g. platinum plate, spongy platinum, platinum black, colloidal platinum, platinum oxide, platinum wire, etc.), and the like.

This reaction is usually carried out in a conventional solvent which does not adversely influence the reaction such as water, alcohol (e.g. methanol, ethanol, propanoyl, etc.), dioxane, tetrahydrofuran, acetic acid, buffer solution (e.g. phosphate buffer, acetate buffer, etc.), and the like, or a mixture thereof.

The reaction temperature is not critical and the reaction is usually carried out under from cooling to warming.

(3) Process 3

The compound (I-a) or a salt thereof can be prepared by reacting the compound (III) or a salt thereof with ammonia or a salt thereof.

Suitable salts of the compound (III) may be the same as those for the compound (I).

Suitable salts of ammonia may include acid addition salts as mentioned for the compound (I).

The reaction is usually carried out in a conventional solvent which does not adversely influence the reaction such as water, acetone, dichloromethane, alcohol (e.g. methanol, ethanol, etc.), tetrahydrofuran, pyridine, N,N-dimethylformamide, etc., or a mixture thereof.

The reaction temperature is not critical and the reaction is usually carried out under from cooling to heating.

(4) Process 4

The compound (I-e) or a salt thereof can be prepared by subjecting the compound (I-d) or a salt thereof to a removal reaction of the carboxy-protective group in $R_c^1$.

Suitable salts of the compounds (I-d) and (I-e) may be the same as those for the compound (I).

The present reaction is usually carried out by a conventional method such as hydrolysis, reduction, and the like.

(i) Hydrolysis

The hydrolysis is preferably carried out in the presence of a base or an acid. Preferable base may include an alkalimetal hydroxide (e.g. sodium hydroxide, potassium hydroxide, etc.), an alkaline earth metal hydroxide (e.g. magnesium hydroxide, calcium hydroxide, etc.), alkali metal hydride (e.g. sodium hydride, potassium hydride, etc.), alkaline earth metal hydride (e.g. calcium hydride, etc.), alkali metal alkoxide (e.g. sodium methoxide, sodium ethoxide, potassium t-butoxide, etc.), an alkali metal carbonate (e.g. sodium carbonate, potassium carbonate, etc.), and alkaline earth metal carbonate (e.g. magnesium carbonate, calcium carbonate, etc.), an alkali metal bicarbonate (e.g. sodium bicarbonate, potassium bicarbonate, etc.), and the like.

Preferable acid may include an organic acid (e.g. formic acid, acetic acid, propionic acid, trifluoroacetic acid, benzenesulfonic acid, p-toluenesulfonic acid, etc.) and an inorganic acid (e.g. hydrochloric acid, hydrobromic acid, sulfuric acid, phosphoric acid, etc.). The acidic hydrolysis using trifluoroacetic acid is usually accelerated by addition of cation trapping agent (e.g. phenol, anisole, etc.).

This reaction is usually carried out in a conventional solvent which does not adversely influence the reaction such as water, dichloromethane, alcohol (e.g. methanol, ethanol, etc.), tetrahydrofuran, dioxane, acetone, etc., or a mixture thereof. A liquid base or acid can be also used as the solvent.

The reaction temperature is not critical and the reaction is usually carried out under from cooling to heating.

(ii) Reduction

The reduction method applicable for this removal reaction may include, for example, reduction by using a combination of a metal (e.g. zinc, zinc amalgam, etc.) or a slat of chrome compound (e.g. chromous chloride, chromous acetate, etc.) and an organic or inorganic acid (e.g. acetic acid, propionic acid, hydrochloric acid, sulfuric acid, etc.); conventional catalytic reduction in the presence of a conventional metallic catalyst such as palladium catalysts (e.g. spongy palladium, palladium black, palladium oxide, palladium on carbon, colloidal palladium, palladium on barium sulfate, palladium on barium carbonate, palladium hydroxide on carbon, etc.), nickel catalysts (e.g. reduced nickel, nickel oxide, Raney nickel, etc.), platinum catalysts (e.g. platinum plate, spongy platinum, platinum black, colloidal platinum, platinum oxide, platinum wire, etc.); sodium boro hydride; lithium aluminum hydride; and the like.

In case that the catalytic reduction is applied, the reaction is preferably carried out around neutral condition.

This reaction is usually carried out in a conventional solvent which does not adversely influence the reaction such as water, alcohol (e.g. methanol, ethanol, propanol, etc.), dioxane, tetrahydrofuran, acetic acid, buffer solution (e.g. phosphate buffer, acetate buffer, etc.), and the like, or a mixture thereof.

The reaction temperature is not critical and the reaction is usually carried out under from cooling to warming.

(5) Process 5

The compound (I-g) or a salt thereof can be prepared by subjecting the compound (I-f) or a salt thereof to a removal reaction of the carboxy-protective group in $R_a^2$.

Suitable salts of the compounds (I-f) and (I-g) may be the same as those for the compound (I).

The present reaction is usually carried out in substantially the same manner as that of Process 4, therefore, the reaction conditions (e.g. temperature, solvents, etc.) can be referred to the explanation of Process 4.

(6) Process 6

The compound (I-h) or a salt thereof can be prepared by introducing an amidino-protective group into the compound (I-a) or a salt thereof.

Suitable salts of the compound (I-h) may be the same as those for the compound (I).

Suitable introducing agent of the amidino-protective group used in this reaction may be a conventional agent which is capable of introducing the amidino-protective group as mentioned before such as carboxylic acid, carbonic acid, sulfonic acid and their reactive derivative, for example, an acid halide, an acid anhydride, an activated amide, an activated ester, and the like. Preferable example of such reactive derivative may include acid chloride, acid bromide, a mixed acid anhydride with an acid such as substituted phosphoric acid (e.g. dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, sulfuric acid, alkyl carbonate (e.g. methyl carbonate, ethyl carbonate, propyl carbonate, etc.), aliphatic carboxylic acid (e.g. pivalic acid, pentanoic acid, isopentanoic acid, 2-ethylbutyric acid, trichloroacetic acid, etc.), aromatic carboxylic acid (e.g., benzoic acid, etc.), a symmetrical acid anhydride, an activated acid amide with a heterocyclic compound containing imino function such as imidazole, 4-substituted imidazole, dimethylpyrazole, triazole and tetrazole, an activated ester (e.g. p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyridyl ester, piperidinyl ester, 8-quinolyl thioester, or an ester with a N-hydroxy compound such as N,N-dimethylhydroxylamine, 1-hydroxy-2-(1H)-pyridone, N-hydroxysuccinimide, N-hydroxyphthalimide, 1-hydroxybenzotriazole, 1-hydroxy-6-chlorobenzotriazole, etc.), and the like.

This reaction can be carried out in the presence of an organic or inorganic base such as alkali metal (e.g. lithium, sodium, potassium, etc.), alkaline earth metal (e.g. calcium, etc.), alkali metal hydride (e.g. sodium hydride, etc.), alkaline earth metal hydride (e.g. calcium hydride, etc.), alkali metal hydroxide (e.g. sodium hydroxide, potassium hydroxide, etc.), alkali metal carbonate (e.g. sodium carbonate, potassium carbonate, etc.), alkali metal bicarbonate (e.g. sodium bicarbonate, potassium bicarbonate, etc.), alkali metal alkoxide (e.g. sodium methoxide, sodium ethoxide, potassium tert-butoxide, etc.), alkali metal alkanoic acid (e.g. sodium acetate, etc.), trialkylamine (e.g. triethylamine, etc.), pyridine compound (e.g. pyridine, lutidine, picoline, 4-dimethylaminopyridine, etc.), quinoline, and the like.

In case that the introducing agent is used in a free form or its salt in this reaction, the reaction is preferably carried out in the presence of a condensing agent such as a carbodiimide compound [e.g. N,N'-dicyclohexylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, etc.], a ketenimine compound (e.g. N,N'-carbonylbis(2-methylimidazole), pentamethyleneketene-N-cyclohexylimine, diphenylketene-N-cyclohexylimine, etc.); an olefinic or acetylenic ether compounds (e.g. ethoxyacetylene, β-chlorovinylethyl ether), a sulfonic acid ester of N-hydroxybenzotriazole derivative [e.g. 1-(4-chlorobenzenesulfonyloxy)-6-chloro-1H-benzotriazole, etc.], a combination of trialkylphosphite or triphenylphosphine and carbon tetrachloride, disulfide or diazenedicarboxylate (e.g. diethyl diazenedicarboxylate, etc.), a phosphorus compound (e.g. ethyl polyphosphate, isopropyl polyphosphate, phosphoryl chloride, phosphorus trichloride, etc.), thionyl chloride, oxalyl chloride, N-ethylbenzisoxazolium salt, N-ethyl-5-phenylisoxazolium-3-sulfonate, a reagent (referred to a so-called "Vilsmeier reagent") formed by the reaction of an amide compound such as N,N-di(lower)alkylformamide (e.g. dimethylformamide, etc.), N-methylformamide or the like with a halogen compound such as thionyl chloride, phosphoryl chloride, phosgene or the like.

The reaction is usually carried out in a conventional solvent which does not adversely influence the reaction such as water, acetone, dichloromethane, alcohol (e.g. methanol, ethanol, etc.), tetrahydrofuran, pyridine, N,N-dimethylformamide, etc., or a mixture thereof.

The reaction temperature is not critical and the reaction is usually carried out under from cooling to heating.

(7) Process 7

The compound (I-i) or a salt thereof can be prepared by reacting the compound (I-g) or its reactive derivative at the carboxy group, with N-(lower)alkyl-N-(lower)alkoxyamine or a salt thereof.

Suitable salts of the compound (I-i) may be the same as those for the compound (I).

Suitable salts of N-(lower)alkyl-N-(lower)alkoxyamine may be the same acid addition salts as mentioned for the compound (I).

Suitable reactive derivative at the carboxy group of the compound (I-g) may include an acid halide, an acid anhydride, an activated amide, an activated ester, and the like. Suitable examples of the reactive derivatives may be an acid chloride; an acid azide; a mixed acid anhydride with acid such as substituted phosphoric acid [e.g. dialkylphosphoric acid, phenylphosphoric acid, diphenylphosphoric acid, dibenzylphosphoric acid, halogenated phosphoric acid, etc.], dialkylphosphorous acid, sulfurous acid, thiosulfuric acid, sulfuric acid, sulfonic acid [e.g. methanesulfonic acid, etc.], aliphatic carboxylic acid [e.g. acetic acid, propionic acid, butyric acid, isobutyric acid, pivalic acid, pentanoic acid, isopentanoic acid, 2-ethylbutyric acid, trichloroacetic acid, etc.] or aromatic carboxylic acid [e.g. benzoic acid, etc.]; a symmetrical acid anhydride; an activated amide with imidazole, 4-substituted imidazole, dimethylpyrazole, triazole or tetrazole; or an activated ester [e.g. cyanomethyl ester, methoxymethyl ester, dimethyliminiomethyl $[(CH_3)_2$ $$[(CH_3)_2\overset{+}{N}{=\!\!=}CH{-\!\!-}]$$

$={CH}{-\!\!-}$] ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.], or an ester with a N-hydroxy compound [e.g. N,N-dimethylhydroxylamine, 1-hydroxy-2-(1H)-pyridone, N-hydroxysuccinimide, N-hydroxyphthalimide, 1-hydroxy-1H-benzotriazole, etc.], and the like. These reactive derivatives can optionally be selected from them according to the kind of the compound (I-g) to be used.

The reaction is usually carried out in a conventional solvent such as water, alcohol [e.g. methanol, ethanol, etc.], acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction. These conventional solvent may also be used in a mixture with water.

In this reaction, when the compound (II) is used in a free acid form or its salt form, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide, N,N'-diisopropylcarbodiimide; N-ethyl-N'-(3-dimethylaminopropyl)carbodiimide; N,N'-carbonylbis(2-methylimidazole); pentamethyleneketene-N-cyclohexylimine; diphenylketene-N-cyclohexylimine; ethoxyacetylene; 1-alkoxy-1-chloroethylene; trialkyl phosphite; O-benzotriazol-1-yl-N,N,N',N'-tetramethylurenium hexafluorophosphate; ethyl polyphosphate; isopropyl polyphosphate; phosphorus oxychloride (phosphoryl chloride); phosphorus trichloride; diphenyl phosphorylazide; thionyl chloride; oxalyl chloride; lower alkyl haloformate [e.g. ethyl chloroformate, isopropyl chloroformate, etc.]; triphenylphosphine; 2-ethyl-7-hydroxybenzisoxazolium salt; 2-ethyl-5-(m-sulfophenyl)isoxazolium hydroxide intramolecular salt; N-hydroxybenzotriazole; 1-(p-chlorobenzenesulfonyloxy)-6-chloro-1H-benzotriazole; so-called Vilsmeier reagent prepared by the reaction of N,N-dimethylformamide with thionyl chloride, phosgene, trichloromethyl chloroformate, phosphorus oxychloride, etc.; or the like.

The reaction may also be carried out in the presence of an inorganic or organic base such as an alkali metal bicarbonate, tri(lower)alkylamine (e.g. triethylamine, etc.), pyridine, N-(lower)alkylmorpholine, N,N-di(lower) alkylbenzyl-amine, or the like.

The reaction temperature is not critical and the reaction is usually carried out under cooling to warming.

(8) Process 8

The compound (I-a) or a salt thereof can be prepared by subjecting the compound (I-h) or a salt thereof to a removal reaction of the amidino-protective group of $R_a^3$.

The present reaction is usually carried out in substantially the same manner as that of Process 4, therefore, the reaction conditions (e.g. temperature, solvents, etc.) can be referred to the explanation of Process 4.

(9) Process 9

The compound (I-k) or a salt thereof can be prepared by reducing the compound (I-j) or a salt thereof.

Suitable salts of the compounds (I-j) and (I-k) may be the same as those for the compound (I).

The present reaction is usually carried out in substantially the same reduction reaction as that of Process 4, therefore, the reaction conditions (e.g. temperature, solvents, etc.) can be referred to the explanation of Process 4.

[Urokinase Inhibiting Effect]

Now in order to show the utility of the object compound (I) and pharmaceutically acceptable salts, the test datum on urokinase inhibiting effect of the representative compound of the compound (I) of this invention is shown in the following.

Test Compound

Compound A [The product of Example 2-1)]

Test Method

Test Compound was incubated at desired concentrations with 25 International Units (IU)/ml human high molecular weight urokinase (Fujisawa Pharmaceutical Co., Ltd.) and urokinase substrate (S-2288, H-D-Isoleucyl-L-prolyl-L-arginine-p-nitroaniline dihydrochloride; Chromagenix, Sweden; Japan distributors Daiichikagakuyakuhin Co., Ltd.) in a 100 $\mu l$ final volume of 50 mM Tris, 100 mM NaCl, 1 mM Na$_2$EDTA, 0.01% (v/v) polyoxyethylenesorbitan monooleate (Tween 80), pH 7.5 (Buffer Z). Incubations were carried out at 37° C. for 30 minutes. Color was quantitated by measuring absorbance at 405 nm (A$_{405}$) using EL312 Automated Microplate Reader.

Test Result

| Test Compound | IC$_{50}$ ($\mu M$) |
| --- | --- |
| Compound A | 0.47 |

For therapeutic administration, the object compound (I) and the pharmaceutically acceptable salts thereof of the present invention are used in the form of conventional pharmaceutical preparation which contains said compound, as an active ingredient, in admixture with pharmaceutically acceptable carriers such as an organic or inorganic solid or liquid excipient which is suitable for oral, parenteral and external administration. The pharmaceutical preparations may be in solid form such as tablet, granule, powder, capsule, or liquid form such as solution, suspension, syrup, emulsion, lemonade, and the like.

If needed, there may be included in the above preparations auxiliary substances, stabilizing agents, wetting agents and other commonly used additives such as lactose, stearic acid, magnesium stearate, terra alba, sucrose, corn starch, talc, gelatin, agar, pectin, peanut oil, olive oil, cacao butter, ethylene glycol, tartaric acid, citric acid, fumaric acid, and the like.

While the dosage of the compound (I) may vary from and also depend upon the age, condition of the patient, a kind of diseases, a kind of the compound (I) to be applied, etc. In general, amount between about 0.001 mg and about 300 mg, preferably about 0.1 mg to about 50 mg per day may be administered to a patient. An average single dose of about 0.001 mg, 0.01 mg, 0.03 mg, 0.1 mg, 0.3 mg, 0.6 mg, 1.0 mg, 3.0 mg, 10.0 mg, 50.0 mg, 100.0 mg of the object compound (I) of the present invention may be used.

The following Preparations and Examples are given for the purpose of illustrating this invention in more detail.

Preparation 1-1)

Diethyl ethoxycarbonylmethylphosphonate (8.47 ml) was dropwise added to a mixture of sodium hydride (60%, 1.71 g) and tetrahydrofuran (THF) (50 ml) at room temperature (r.t.) under nitrogen atmosphere, and the mixture was stirred under the same condition for 30 minutes. To the reaction mixture was added 4-oxo-4,5,6,7-tetrahydrobenzo[b]thiophene (5.00 g) in a portion, and the whole mixture was stirred at r.t. for 3 hours. The reaction mixture was poured into a mixture of water and ethyl acetate (AcOEt). The separated organic layer was washed with water and brine, and dried over magnesium sulfate ($MgSO_4$), and dried in vacuo to precipitate. The resulting precipitate was washed with isopropyl ether (iPE) to give 4-ethoxycarbonylmethylidene-4,5,6,7-tetrahydrobenzo[b]thiophene (5.91 g).

IR (Nujol): 1700, 1605 $cm^{-1}$
MASS (z/e): 223 $(M+H)^+$
NMR (DMSO-$d_6$, δ): 1.31 (3H, t, J=7.1 Hz), 2.01 (2H, m), 2.89 (2H, t, J=7.1 Hz), 3.15 (2H, m), 4.19 (2H, t, J=7.1 Hz), 5.67 and 6.11 (1H, each s), 7.06 (1H, d, J=5.4 Hz), 7.20 (1H, d, J=5.4 Hz)

Preparation 1-2)

The following compound was obtained according to a similar manner to that of Preparation 3-3).

4-Carboxymethylidene-4,5,6,7-tetrahydrobenzo[b]thiophene

NMR (DMSO-$d_6$, δ): 1.84 (2H, tt, J=5.7, 6.1 Hz), 2.85 (2H, t, J=6.1 Hz), 3.03 (2H, t, J=5.7 Hz), 6.14 (1H, s), 7.33 (1H, d, J=5.4 Hz), 7.39 (1H, d, J=5.4 Hz), 11.99 (1H, br s)

Preparation 1-3)

To a mixture of 4-carboxymethylidene-4,5,6,7-tetrahydrobenzo[b]thiophene (0.50 g), n-butylamine (0.28 ml), 1-hydroxybenzotriazole (0.43 g) and dimethylformamide (DMF) (5 ml) was added 1-(3-dimethylaminopropyl)-3-ethylcarbodiimide hydrochloride (0.54 g). The reaction mixture was stirred at r.t. for 5 hours and poured into a mixture of AcOEt and a saturated aqueous solution of sodium hydrogen carbonate ($NaHCO_3$). The separated organic layer was washed with water and brine, and dried over $MgSO_4$, and evaporated to give 4-(N-butylcarbamoyl)methylidene-4,5,6,7-tetrahydrobenzo[b]thiophene (0.60 g).

MASS (z/e): 250 $(M+H)^+$
NMR (DMSO-$d_6$, δ): 0.88 (3H, t, J=7.2 Hz), 1.2–1.4 (4H, m), 1.7–1.9 (2H, m), 2.82 (2H, d, J=6.0 Hz), 3.0–3.2 (4H, m), 6.21 (1H, s), 7.18 (1H, d, J=5.4 Hz), 7.33 (1H, d, J=5.4 Hz), 7.84 (1H, br s)

Preparation 1-4)

To a mixture of 4-(N-butylcarbamoyl)methylidene-4,5,6,7-tetrahydrobenzo[b]thiophene (0.49 g) and THF (8 ml) was dropwise added 1.64 M n-butyl lithium (n-BuLi) in n-hexane (2.88 ml) at −70~−60° C. under nitrogen atmosphere and the mixture was stirred under the same condition for 2.5 hours. The reaction mixture was poured into a mixture of dry ice and diethyl ether ($Et_2O$). To the mixture were added $Et_2O$ and water. The separated aqueous layer was washed with $Et_2O$, and acidified by 6 N hydrochloric acid (HCl) and was extracted with AcOEt. The organic layer was washed with water and brine, and dried over $MgSO_4$, and evaporated in vacuo to give 4-(N-butylcarbamoyl)methylidene-4,5,6,7-tetrahydrobenzo[b]thiophene-2-carboxylic acid (0.38 g).

This product was used in the following reaction without isolation.

Preparation 1-5)

A mixture of 4-(N-butylcarbamoyl)methylidene-4,5,6,7-tetrahydrobenzo[b]thiophene-2-carboxylic acid (0.57 g), conc. sulfuric acid ($H_2SO_4$) (3 ml), and methanol (MeOH) (15 ml) was stirred at reflux for 1.5 hours. The reaction mixture was poured into a mixture of AcOEt and water. The organic layer was washed with saturated aqueous solution of $NaHCO_3$, water and brine, and dried over $MgSO_4$, and evaporated in vacuo. After evaporation, the resulting oil was purified by chromatography on silica gel (AcOEt-n-hexane as an eluent). The fractions including the object compound were collected and evaporated to give 4-(N-butylcarbamoyl) methylidene-2-methoxycarbonyl-4,5,6,7-tetrahydrobenzo[b]thiophene (115.3 mg).

NMR (DMSO-$d_6$, δ): 0.89 (3H, t, J=6.9 Hz), 1.2–1.6 (4H, m), 1.7–2.0 (2H, m), 2.78 (2H, t, J=6.0 Hz), 3.0–3.2 (4H, m), 3.82 (3H, s), 6.39 (1H, s), 7.78 (1H, t, J=5.5 Hz), 7.89 (1H, s)

Preparation 2-1)

The following compound was obtained according to a similar manner to that of Preparation 4-1).

4-n-Butylidene-4,5,6,7-tetrahydrobenzo[b]thiophene

MASS (z/e): 193 $(M+H)^+$
NMR ($CDCl_3$, δ): 0.9–1.0 (3H, m), 1.3–1.6 (2H, m), 1.7–2.9 (8H, m), 5.5 and 5.8 (1H, t, J=7.4 Hz), 6.9–7.2 (2H, m)

Preparation 2-2)

The following compound was obtained according to a similar manner to that of Preparation 1-4).

4-n-Butylidene-2-carboxy-4,5,6,7-tetrahydrobenzo[b]thiophene

MASS (z/e): 237 $(M+H)^+$
NMR ($CDCl_3$, δ): 0.85 (3H, t, J=6.5 Hz), 0.9–2.0 (8H, m), 2.6–3.0 (2H, m), 4.83 (1H, s), 7.61 (1H, s), 12.83 (1H, br s)

Preparation 2-3)

The following compound was obtained according to a similar manner to that of Preparation 4-3).

4-n-Butylidene-2-methoxycarbonyl-4,5,6,7-tetrahydrobenzo[b]thiophene

IR (Neat): 2954, 2866, 1713, 1543 $cm^{-1}$
NMR (DMSO-$d_6$, δ): 0.8–1.0 (3H, m), 1.2–3.0 (10H, m), 3.80 (3H, s), 5.62 and 5.97 (1H, each t, J=7.2 Hz), 7.64 and 7.93 (1H, each s)

Preparation 3-1)

The following compound was obtained according to a similar manner to that of Preparation 1-1).

Ethyl 5-(2-thienyl)-2,4-pentadienoate

NMR ($CDCl_3$, δ): 1.30 (3H, t, J=7.1 Hz), 4.23 (2H, q, J=7.1 Hz), 5.94 (1H, d, J=15.2 Hz), 6.66 (1H, dd, J=15.2, 11.1 Hz), 7.0–7.6 (5H, m)

Preparation 3-2)

A mixture of ethyl 5-(2-thienyl)-2,4-pentdienoate (20.20 g), 10% palladium hydroxide (Pd(OH)$_2$) (2.04 g), THF (200 ml), MeOH (100 ml) and 1 N HCl (10 ml) was stirred at r.t. under nitrogen atmosphere for 3.5 hours. After removal of insoluble solids, the filtrate was evaporated in vacuo, and the residue was dissolved with a mixture of AcOEt and water. The organic layer was washed with saturated aqueous solution of NaHCO$_3$, water and brine, and dried over MgSO$_4$, and evaporated in vacuo to give ethyl 5-(2-thienyl) pentanoate (15.70 g).

MASS (z/e): 211 (M-H)$^+$

NMR (DMSO-d$_6$, δ): 1.25 (3H, m), 1.4–3.0 (8H, m), 4.2 (2H, m), 6.8–7.2 (3H, m)

Preparation 3-3)

A mixture of ethyl 5-(2-thienyl)pentanoate (15.40 g), sodium hydroxide (NaOH) (2.90 g), water (H$_2$O) (18 ml), and tetrahydrofuran (THF) (100 ml) was stirred at reflux for 2.5 hours. The reaction mixture was poured into a mixture of water and diethyl ether (Et$_2$O). The aqueous layer was separated, and acidified with 6 N hydrochloric acid (HCl), and extracted with ethyl acetate (AcOEt). The organic layer was washed with water and brine, and dried over magnesium sulfate (MgSO$_4$), and evaporated to give 5-(2-thienyl) pentanoic acid (12.07 g) as an oil.

NMR (CDCl$_3$, δ): 1.6–3.0 (8H, m), 6.9–7.2 (3H, m)

Preparation 3-4)

To a mixture of 5-(2-thienyl)pentanoic acid (5.04 g) and toluene (50 ml) was dropwise added trifluoroacetic anhydride (6.95 ml) over 1 minute with ice-water cooling. The reaction mixture was stirred at room temperature (r.t.) overnight, and was poured into a mixture of a saturated aqueous solution of sodium hydrogen carbonate (NaHCO$_3$) and AcOEt. The organic layer was washed with water and brine, and dried over MgSO$_4$, and evaporated. The resulting oil was purified by chromatography on silica gel (SiO$_2$) (20% AcOEt in n-hexane as eluent). The fractions including the object compound were combined and evaporated to give 4-oxo-5,6,7,8-tetrahydro-4H-cyclohepta[b]thiophene (1.57 g) as an oil.

MASS (z/e): 167 (M+H)$^+$

NMR (CDCl$_3$, δ): 1.90 (2H, m), 2.70 (2H, m), 3.10 (2H, m), 6.98 (1H, d, J=5.3 Hz), 7.41 (1H, d, J=5.3 Hz)

Preparation 3-5)

A mixture of sodium hydride (NaH) (60% in Nujol, 0.69 g) and dimethyl sulfoxide (DMSO) (9 ml) was stirred at 70° C. for 2 hours. After cooling to r.t., THF (6 ml) and n-butyl-triphenylphosphonium bromide (7.26 g) were added thereto. The reaction mixture was stirred at r.t. for 1 hour, and then 4-oxo-5,6,7,8-tetrahydro-4H-cyclohepta[b]thiophene (1.44 g) was added. The mixture was stirred at r.t. overnight and poured into a mixture of a saturated aqueous solution of ammonium chloride (NH$_4$Cl) and AcOEt. The separated organic layer was washed with water and brine, and dried over MgSO$_4$, and evaporated. The resulting oil was purified by chromatography on SiO$_2$ (1% AcOEt in n-hexane as eluent). The fractions containing the object compound were combined and evaporated to give 4-n-butylidene-5,6,7,8-tetrahydro-4H-cyclohepta[b]thiophene (1.15 g) as an oil.

MASS (z/e): 251 (M+H)$^+$

NMR (CHCl$_3$, δ): 0.7–3.0 (15H, m), 5.44 and 5.59 (1H, each t, J=7.4 Hz each), 6.8–7.0 (2H, m)

Preparation 3-6)

The following compound was obtained according to a similar manner to that of Preparation 4-2).

4-n-Butylidene-5,6,7,8-tetrahydro-4H-cyclohepta[b]thiophene-2-carboxylic acid

MASS (z/e): 251 (M+H)$^+$

NMR (DMSO-d$_6$, δ): 0.8–3.0 (15H, m), 5.51 and 5.62 (1H, each t, J=7.3 and 7.4 Hz), 7.59 and 7.68 (1H, each s)

Preparation 3-7)

N-Methylmorpholine (0.69 ml) was added to a mixture of 4-n-butylidene-5,6,7,8-tetrahydro-4H-cyclohepta[b]thiophene-2-carboxylic acid (1.05 g) and THF (10 ml) at −15~−20° C. under nitrogen atmosphere, and isobutyl chloroformate (0.82 ml) was added thereto over 2 minutes. The mixture was stirred under the same condition for 30 minutes, and conc. ammonia (c.NH$_3$) was added thereto. The mixture was stirred at r.t. for 2 hours. The reaction mixture was poured into a mixture of water and AcOEt to precipitate. The precipitate was collected by filtration, washed with water and Et$_2$0, and dried in vacuo to give 4-n-butylidene-5,6,7,8-tetrahydro-4H-cyclohepta[b]thiophene-2-carboxamide (0.59 g).

NMR (CDCl$_3$, δ): 0.8–3.0 (15H, m), 5.48 and 5.59 (1H, each t, J=7.3 and 7.3 Hz), 5.77 (2H, br s), 7.27 and 7.35 (1H, each s)

Preparation 3-8)

Phosphorus oxychloride (0.30 ml) was added to a mixture of 4-n-butylidene-5,6,7,8-tetrahydro-4H-cyclohepta[b]thiophene-2-carboxamide (0.55 g) and dimethylformamide (DMF) (6 ml) with ice-water cooling under nitrogen atmosphere, and the mixture was stirred under the same condition for 1 hour. The reaction mixture was poured into an ice-cooled mixture of an aqueous solution of NaHCO$_3$ and AcOEt to precipitate. The precipitate was collected by filtration, washed with water, and dried in vacuo to give 4-n-butylidene-5,6,7,8-tetrahydro-2-cyano-4H-cyclohepta[b]thiophene (0.42 g), which was immediately used in the next reaction.

IR (KBr): 2929, 2863, 2213, 1710, 1679, 1616 cm$^{-1}$

Preparation 3-9)

The following compound was obtained according to a similar manner to that of Preparation 5-2).

4-n-Butylidene-2-(1-ethoxy-1-iminomethyl)-5,6,7,8-tetrahydro-4H-cyclohepta[b]thiophene, which was used in the following reaction without isolation.

Preparation 4-1)

To a mixture of 4-oxo-4,5,6,7-tetrahydrobenzo[b]furan (20.06 g) and THF (200 ml) was added dropwise 2M n-butylmagnesium bromide with ice-water cooling over 15 minutes. The mixture was stirred at r.t. overnight. The reaction mixture was poured into a mixture of a saturated aqueous solution of NH$_4$Cl and AcOEt. The separated organic layer was washed with water and brine, and dried over MgSO$_4$, and evaporated. The resulting oil was purified by chromatography on SiO$_2$ (CHCl$_3$ as eluent) to give 4-n-butylidene-4,5,6,7-tetrahydrobenzo[b]furan as a yellow oil (12.06 g).

NMR (CDCl$_3$, δ): 0.85 (3H, m), 1.2–2.8 (10H, m), 5.28 and 5.51 (1H, t, J=7.4 Hz), 6.2–6.4 (1H, m), 7.2–7.3 (1H, m)

Preparation 4-2)

To a mixture of 1.66 N n-butyl lithium (nBuLi) (328 ml in n-hexane solution) and Et$_2$O (100 ml) was added a mixture of 4-n-butylidene-4,5,6,7-tetrahydrobenzo[b]furan (9.60 g) and Et$_2$O (50 ml) dropwise over 5 minutes while maintaining −30~−20° C. by dry ice—carbon tetrachloride (CCl$_4$) cooling. The reaction mixture was stirred at r.t. for 1 hour, and was bubbled by carbon dioxide (CO$_2$) gas for 1 hour. The whole mixture was stirred at r.t. overnight and poured into a mixture of water and Et$_2$O. The separated aqueous layer was adjusted to pH 1.4 with 10% HCl, and extracted by AcOEt. The orgaic layer was washed with brine, dried over $MgSO_4$, and evaporated to give 4-n-butylidene-4,5,6,7-tetrahydrobenzo[b]furan-2-carboxylic acid (3.91 g) as a reddish oil, which was used in the next reaction without further purification.

Preparation 4-3)

A mixture of 4-n-butylidene-4,5,6,7-tetrahydrobenzo[b]furan-2-carboxylic acid (3.91 g) obtained in Preparation 4-2), conc. sulfuric acid ($H_2SO_4$) (10 ml), and methanol (MeOH) (100 ml) was stirred at reflux for 1.5 hours. After being concentrated in vacuo to remove MeOH, the resulting mixture was poured into a mixture of AcOEt and water. The separated organic layer was washed with water and brine, dried over $MgSO_4$, and evaporated. The resulting oil was purified by chromatography on $SiO_2$ (7% AcOEt in n-hexane as eluent) to give 4-n-butylidene-2-methoxycarbonyl-4,5,6,7-tetrahydrobenzo[b]furan (1.72 g) as an oil.

MASS (z/e): 235 $(M+H)^+$

NMR ($CDCl_3$, δ): 0.93 (3H, t, J=7.4 Hz), 1.40 (2H, m), 1.85 (2H, m), 2.15 (2H, q, J=7.4 Hz), 2.40 (2H, m), 2.74 (2H, t, J=7.4 Hz), 3.88 and 3.90 (3H, each s), 5.25 and 5.61 (1H, each t, J=7.5 Hz), 7.26 (1H, s)

Preparation 5-1)

To a solution of 1-n-butyl-6-cyano-2-oxo-2,3-dihydro-1H-thieno[2,3-b][1,4]thiazine (0.43 g) in chloroform (15 ml) was added m-chloroperbenzoic acid (0.88 g) under ice cooling. After stirring for 22 hours at room temperature, the reaction mixture was poured into a mixture of ethyl acetate and saturated aqueous sodium thiosulfate. The organic layer was successively washed with 20% aqueous potassium carbonate, water and brine and dried over magnesium sulfate. The solvent was evaporated in vacuo and the residue was purified by column chromatography on silica gel eluting with chloroform. The fractions containing the object compound were collected and evaporated in vacuo to give 1-n-butyl-6-cyano-2-oxo-2,3-dihydro-1H-thieno[2,3-b][1,4]thiazine 1,1-dioxide (0.32 g).

IR (Nujol): 2220, 1685, 1540 $cm^{-1}$

NMR (DMSO-$d_6$, δ): 0.88 (3H, t, J=7.2 Hz), 1.1–1.6 (4H, m), 3.9–4.1 (2H, m), 5.04 (2H, s), 8.38 (1H, s)

Preparation 5-2)

A mixture of 1-n-butyl-6-cyano-2-oxo-2,3-dihydro-1H-thieno[2,3-b][1,4]thiazine 1,1-dioxide (0.30 g) and ethanol (EtOH) (15 ml) was bubbled with hydrogen chloride under ice-water cooling for 15 minutes. After being saturated with hydrogen chloride, the mixture was stood at r.t. for 3 hours. The reaction mixture was evaporated to give precipitate. The resulting precipitate was washed with IPE to give 1-n-butyl-2-oxo-2,3-dihydro-6-(1-ethoxy-1-iminomethyl)-1H-thieno[2,3][1,4]thiazine hydrochloride (0.32 g).

IR (Nujol): 1685, 1630 $cm^{-1}$ (+) APCI MASS: 331 $(M+H)^+$

NMR (DMSO-$d_6$, δ): 0.8–1.0 (3H, m), 1.2–1.7 (7H, m), 3.8–4.1 (2H, m), 4.53 (2H, q, J=7.0 Hz), 5.04 (2H, s), 8.80 (1H, s)

Preparation 6-1)

The following compound was obtained according to a similar manner to that of Preparation 15-6).

1-n-Butyl-2,3-dihydro-6-methoxycarbonyl-2-oxo-1H-thieno[2,3-b][1,4]thiazine

NMR (DMSO-$d_6$, δ): 0.87 (3H, t, J=7.2 Hz), 1.2–1.6 (4H, m), 3.69 (2H, s), 3.83 (3H, s), 3.9–4.0 (2H, m), 7.78 (1H, s)

Preparation 6-2)

To a solution of 1-n-butyl-2,3-dihydro-6-methoxycarbonyl-2-oxo-1H-thieno[2,3-b][1,4]thiazine (31.9 g) in tetrahydrofuran (300 ml) was added dropwise boran-tetrahydrofuran complex (1.0 M solution in tetrahydrofuran) (294 ml). After stirring for 3 hours at room temperature, the solvent was evaporated in vacuo and the residue was poured into water. The solution was adjusted to pH 8 with 20% aqueous potassium carbonate and extracted with ethyl acetate. The extract was washed with water and brine, and dried over magnesium sulfate. The solvent was evaporated in vacuo and the residue was purified by column chromatography on silica gel eluting with toluene. The fractions containing the object compound were collected and evaporated in vacuo to give 1-n-butyl-2,3-dihydro-6-methoxycarbonyl-1H-thieno-[2,3-b][1,4]thiazine (30.85 g).

IR (Film): 2950, 2850, 1700, 1550 $cm^{-1}$ (+) APCI MASS: 272 $(M+H)^+$

NMR (DMSO-$d_6$, δ): 0.90 (3H, t, J=7.1 Hz), 1.2–1.6 (4H, m), 3.1–3.3 (4H, m), 3.4–3.5 (2H, m), 3.77 (3H, s), 7.37 (1H, s)

Preparation 7-1)

The following compound was obtained according to a similar manner to that of Preparation 15-6).

1-Benzyl-2,3-dihydro-6-methoxycarbonyl-2-oxo-1H-thieno[2,3-b][1,4]thiazine

IR (Nujol): 1720, 1660 $cm^{-1}$

NMR (DMSO-$d_6$, δ): 3.77 (3H, s), 3.85 (2H, s), 5.18 (2H, s), 7.2–7.4 (5H, m), 7.65 (1H, s)

Preparation 7-2)

The following compound was obtained according to a similar manner to that of Preparation 6-2).

1-Benzyl-2,3-dihydro-6-methoxycarbonyl-1H-thieno[2,3-b][1,4]thiazine

IR (Nujol): 1690, 1540 $cm^{-1}$ (+) APCI MASS: 306 $(M+H)^+$

NMR (DMSO-$d_6$, δ) 3.1–3.2 (2H, m), 3.4–3.6 (2H, m), 3.74 (3H, s), 4.47 (2H, s), 7.2–7.5 (6H, m)

Preparation 8-1)

The following compound was obtained according to a similar manner to that of Preparation 15-6) by using 3,4-dimethoxyphenethyl p-toluenesulfonate.

2,3-Dihydro-6-methoxycarbonyl-1-(3,4-dimethoxyphenethyl)-2-oxo-1H-thieno[2,3-b][1,4]thiazine (+) APCI MASS: 394 $(M+H)^+$ NMR (DMSO-$d_6$, δ): 2.6–2.8 (2H, m), 3.6–3.7 (8H, m), 3.81 (3H, s), 4.0–4.2 (2H, m), 6.6–6.9 (3H, m), 7.61 (1H, s)

Preparation 8-2)

The following compound was obtained according to a similar manner to that of Preparation 15-6) by using cyclohexylmethyl bromide.

1-Cyclohexylmethyl-2,3-dihydro-6-methoxycarbonyl-2-oxo-1H-thieno[2,3-b][1,4]thiazine IR (Nujol): 1710, 1655, 1550 $cm^{-1}$ (+) APCI MASS: 326 $(M+H)^+$ NMR (DMSO-$d_6$, δ): 0.8–1.2 (5H, m), 1.4–1.8 (6H, m), 3.69 (2H, s), 3.7–3.9 (5H, m), 7.83 (1H, s)

Preparation 8-3)

The following compound was obtained according to a similar manner to that of Preparation 15-6) by using phenethyl bromide.

2,3-Dihydro-6-methoxycarbonyl-2-oxo-1-phenethyl-1H-thieno[2,3-b][1,4]thiazine (+) APCI MASS: 334 (M+H)$^+$ NMR (DMSO-d$_6$, δ): 2.7–2.9 (2H, m), 3.67 (2H, s), 3.82 (3H, s), 4.0–4.2 (2H, m), 7.1–7.3 (5H, m), 7.68 (1H, s)
Preparation 8-4)

The following compound was obtained according to a similar manner to that of Preparation 15-6) by using 3,4-methylenedioxyphenethyl p-toluenesulfonate.

2,3-Dihydro-6-methoxycarbonyl-1-(3,4-methylenedioxyphenethyl)-2-oxo-1H-thieno[2,3-b][1,4]thiazine (+) APCI MASS: 378 (M+H)$^+$ NMR (DMSO-d$_6$, δ): 2.6–2.8 (2H, m), 3.67 (2H, s), 3.82 (3H, s), 4.0–4.2 (2H, m), 6.5–6.6 (1H, m), 6.75 (1H, d, J=7.9 Hz), 6.79 (1H, d, J=1.4 Hz), 7.64 (1H, s)
Preparation 8-5)

The following compound was obtained according to a similar manner to that of Preparation 15-6) by using benzyl bromide.

1-Benzyl-6-ethoxycarbonyl-2,3-dihydro-2-oxo-1H-thieno[2,3-b][1,4]thiazine

IR (Nujol): 1705, 1645, 1550 cm$^{-1}$ (+) APCI MASS: 334 (M+H)$^+$

NMR (DMSO-d$_6$, δ): 1.24 (3H, t, J=7.1 Hz), 3.85 (2H, s), 4.23 (2H, q, J=7.1 Hz), 5.18 (2H, s), 7.1–7.4 (5H, m), 7.65 (1H, s)

The following compounds were obtained according to a similar manner to that of Preparation 3-3).
Preparation 9-1)

6-Carboxy-2,3-dihydro-1-(3,4-dimethoxyphenethyl)-2-oxo-1H-thieno[2,3-b][1,4]thiazine IR (Nujol): 1690, 1615, 1515 cm$^{-1}$ (+) APCI MASS: 380 (M+H)$^+$ NMR (DMSO-d$_6$, δ): 2.6–2.8 (2H, m), 3.6–3.8 (8H, m), 4.0–4.2 (2H, m), 6.6–6.9 (3H, m), 7.56 (1H, s)
Preparation 9-2)

6-Carboxy-1-cyclohexylmethyl-2,3-dihydro-2-oxo-1H-thieno[2,3-b][1,4]thiazine

IR (Nujol): 1690, 1605, 1545 cm$^{-1}$ (+) APCI MASS: 312 (M+H)$^+$

NMR (DMSO-d$_6$, δ): 0.8–1.3 (5H, m), 1.4–1.8 (6H, m), 3.67 (2H, s), 3.79 (2H, d, J=6.9 Hz), 7.73 (1H, s)
Preparation 9-3)

6-Carboxy-2,3-dihydro-2-oxo-1-phenethyl-1H-thieno[2,3-b][1,4]thiazine

IR (Nujol): 1690, 1615 cm$^{-1}$ (+) APCI MASS: 320 (M+H)$^+$

NMR (DMSO-d$_6$, δ): 2.7–2.9 (2H, m), 3.66 (2H, s), 4.0–4.2 (2H, m), 7.1–7.3 (5H, m), 7.61 (1H, s)
Peparation 9-4)

6-Carboxy-2,3-dihydro-1-(3,4-methylenedioxyphenethyl)-2-oxo-1H-thieno[2,3-b][1,4]thiazine IR (Nujol): 1685, 1605 cm$^{-1}$ (+) APCI MASS: 364 (M+H)$^+$ NMR (DMSO-d$_6$, δ): 2.6–2.8 (2H, m), 3.66 (2H, s), 4.0–4.2 (2H, m), 5.93 (2H, s), 6.59 (1H, dd, J=1.5, 7.9 Hz), 6.75 (1H, d, J=7.9 Hz), 6.79 (1H, d, J=1.5 Hz), 7.56 (1H, s), 13.27 (1H, br s)
Preparation 9-5)

1-Benzyl-6-carboxy-2,3-dihydro-2-oxo-1H-thieno[2,3-b][1,4]thiazine

IR (Nujol): 1690, 1615 cm$^{-1}$ (+) APCI MASS: 306 (M+H)$^+$

NMR (DMSO-d$_6$, δ): 3.84 (2H, s), 5.16 (2H, s), 7.2–7.4 (5H, m), 7.54 (1H, s), 13.27 (1H, br s)
Preparation 10-1)

The following compound was obtained according to a similar manner to that of Preparation 3-7).

6-Carbamoyl-2,3-dihydro-1-(3,4-dimethoxyphenethyl)-2-oxo-1H-thieno[2,3-b][1,4]thiazine IR (Nujol): 1635, 1510 cm$^{-1}$ (+) APCI MASS: 379 (M+H)$^+$ NMR (DMSO-d$_6$, δ): 2.7–2.9 (2H, m), 3.6–3.8 (8H, m), 3.9–4.1 (2H, m), 6.7–6.9 (3H, m), 7.51 (1H, br s), 7.78 (1H, s), 7.97 (1H, br s)

The following compounds were obtained according to a similar manner to that of Preparation 10-1).
Preparation 10-2)

6-Carbamoyl-1-cyclohexylmethyl-2,3-dihydro-2-oxo-1H-thieno[2,3-b][1,4]thiazine

IR (Nujol): 3300, 3170, 1655, 1600 cm$^{-1}$ (+) APCI MASS: 311 (M+H)$^+$

NMR (DMSO-d$_6$, δ): 0.8–1.3 (5H, m), 1.5–1.8 (6H, m), 3.6–3.8 (4H, m), 7.52 (1H, br s), 7.77 (1H, s), 8.00 (1H, br s)
Preparation 10-3)

6-Carbamoyl-2,3-dihydro-2-oxo-1-phenethyl-1H-thieno[2,3-b][1,4]thiazine

IR (Nujol): 3330, 3150, 1675, 1640, 1610, 1545 cm$^{-1}$ (+) APCI MASS: 319 (M+H)$^+$ NMR (DMSO-d$_6$, δ): 2.7–2.9 (2H, m), 3.64 (2H, s), 3.9–4.1 (2H, m), 7.2–7.3 (5H, m), 7.54 (1H, br s), 7.80 (1H, s), 8.04 (1H, br s)
Preparation 10-4)

6-Carbamoyl-2,3-dihydro-1-(3,4-methylenedioxyphenethyl)-2-oxo-1H-thieno[2,3-b][1,4]thiazine IR (Nujol): 1650 cm$^{-1}$ (+) APCI MASS: 363 (M+H)$^+$ NMR (DMSO-d$_6$, δ): 2.7–2.8 (2H, m), 3.64 (2H, s), 3.9–4.1 (2H, m), 5.96 (2H, s), 6.6–6.9 (3H, s), 7.52 (1H, br s), 7.77 (1H, s), 8.00 (1H, br s)
Preparation 10-5)

1-Benzyl-6-carbamoyl-2,3-dihydro-2-oxo-1H-thieno[2,3-b][1,4]thiazine

IR (Nujol): 1650, 1600 cm$^{-1}$ (+) APCI MASS: 305 (M+H)$^+$

NMR (DMSO-d$_6$, δ): 3.78 (2H, s), 5.04 (2H, s), 7.2–7.6 (6H, m), 7.71 (1H, s), 7.89 (1H, br s)

The following compounds were obtained according to a similar manner to that of Preparation 11-5).

Preparation 11-1)

6-Cyano-2,3-dihydro-1-(3,4-dimethoxyphenethyl)-2-oxo-1H-thieno[2,3-b][1,4]thiazine IR (Nujol): 2220, 1670 cm$^{-1}$
(+) APCI MASS: 361 (M+H)$^+$
NMR (DMSO-d$_6$, δ): 2.6–2.8 (2H, m), 3.6–3.8 (8H, m), 4.0–4.2 (2H, m), 6.6–6.9 (3H, m), 7.94 (1H, s)

Preparation 11-2)

6-Cyano-1-cyclohexylmethyl-2,3-dihydro-2-oxo-1H-thieno[2,3-b][1,4]thiazine

IR (Nujol): 2210, 1660 cm$^{-1}$
(+) APCI MASS: 293 (M+H)$^+$
NMR (DMSO-d$_6$, δ): 0.8–1.3 (5H, m), 1.5–1.7 (6H, m), 3.7–3.8 (4H, m), 8.11 (1H, s)

Preparation 11-3)

6-Cyano-2,3-dihydro-2-oxo-1-phenethyl-2H-thieno[2,3-b][1,4]thiazine

IR (Nujol): 2200, 1660 cm$^{-1}$
(+) APCI MASS: 301 (M+H)$^+$
NMR (DMSO-d$_6$, δ): 2.7–2.9 (2H, m), 3.70 (2H, s), 4.0–4.2 (2H, m), 7.1–7.3 (5H, m), 7.98 (1H, s)

Preparation 11-4)

6-Cyano-2,3-dihydro-1-(3,4-methylenedioxyphenethyl)-2-oxo-1H-thieno[2,3-b][1,4]thiazine IR (Nujol): 2210, 1665 cm$^{-1}$
(+) APCI MASS: 345 (M+H)$^+$
NMR (DMSO-d$_6$, δ): 2.6–2.8 (2H, m), 3.69 (2H, s), 3.9–4.1 (2H, m), 5.95 (2H, s), 6.63 (1H, dd, J=1.6, 7.9 Hz), 6.77 (1H, d, J=7.9 Hz), 6.84 (1H, d, J=1.6 Hz), 7.99 (1H, s)

Preparation 11-5)

A mixture of 1-benzyl-6-carbamoyl-2,3-dihydro-2-oxo-1H-thieno[2,3-b][1,4]thiazine (0.18 g) and p-toluenesulfonyl chloride (0.17 g) in pyridine (5 ml) was stirred for 24 hours at room temperature. The reaction mixture was poured into a mixture of ethyl acetate and water, and adjusted to pH 1.5 with concentrated hydrochloric acid. The organic layer was successively washed with water and brine and dried over magnesium sulfate. The solvent was evaporated in vacuo and the residue was purified by column chromatography on silica gel eluting with chloroform. The fractions containing the object compound were collected and evaporated in vacuo to give 1-benzyl-6-cyano-2,3-dihydro-2-oxo-1H-thieno[2,3-b][1,4]thiazine (0.11 g)

IR (Film): 2950, 2220, 1670, 1540 cm$^{-1}$
NMR (DMSO-d$_6$, δ): 3.85 (2H, s), 5.12 (2H, s), 7.2–7.4 (5H, m), 7.95 (1H, s)

The following compounds were obtained according to a similar manner to that of Preparation 5-2).

Preparation 12-1)

2,3-Dihydro-1-(3,4-dimethoxyphenethyl)-6-(1-ethoxy-1-iminomethyl)-2-oxo-1H-thieno[2,3-b][1,4]thiazine hydrochloride IR (Nujol): 1662, 1600 cm$^{-1}$
(+) APCI MASS: 407 (M+H)$^+$
NMR (DMSO-d$_6$, δ): 1.3–1.5 (3H, m), 2.7–2.9 (2H, m), 3.69 (3H, s), 3.74 (2H, s), 3.76 (3H, s), 4.0–4.1 (2H, m), 4.56 (2H, q, J=6.9 Hz), 6.7–7.0 (3H, m), 8.84 (1H, s)

Preparation 12-2)

1-Cyclohexylmethyl-2,3-dihydro-6-(1-ethoxy-1-iminomethyl)-2-oxo-1H-thieno[2,3-b][1,4]thiazine hydrochloride IR (Nujol): 1655, 1600 cm$^{-1}$
(+) APCI MASS: 339 (M+H)$^+$
NMR (DMSO-d$_6$, δ): 0.8–1.3 (5H, m), 1.41 (3H, t, J=6.9 Hz), 1.5–1.8 (6H, m), 3.7–3.8 (4H, m), 4.57 (2H, q, J=6.9 Hz), 8.81 (1H, s)

Preparation 12-3)

2,3-Dihydro-6-(1-ethoxy-1-iminomethyl)-2-oxo-1-phenethyl-1H-thieno[2,3-b][1,4]thiazine hydrochloride IR (Nujol): 1665, 1610 cm$^{-1}$
(+) APCI MASS: 347 (M+H)$^+$
NMR (DMSO-d$_6$, δ): 1.42 (3H, t, J=6.9 Hz), 2.8–2.9 (2H, m), 3.9–4.1 (2H, m), 4.57 (2H, q, J=6.9 Hz), 7.1–7.4 (5H, m), 8.73 (1H, s)

Preparation 12-4)

2,3-Dihydro-6-(1-ethoxy-1-iminomethyl)-1-(3,4-methylenedioxyphenethyl)-2-oxo-1H-thieno[2,3-b][1,4]thiazine hydrochloride IR (Nujol): 1695, 1670 cm$^{-1}$
(+) APCI MASS: 391 (M+H)$^+$
NMR (DMSO-d$_6$, δ): 1.42 (3H, t, J=7.0 Hz), 2.7–2.9 (2H, m), 3.74 (2H, s), 3.9–4.1 (2H, m), 4.58 (2H, q, J=7.0 Hz), 5.95 (2H, s), 6.6–6.9 (2H, m), 6.94 (1H, d, J=1.3 Hz), 8.77 (1H, s)

Preparation 12-5)

1-Benzyl-2,3-dihydro-6-(1-ethoxy-1-iminomethyl)-2-oxo-1H-thieno[2,3-b][1,4]thiazine hydrochloride (+) APCI MASS: 333 (M+H)$^+$
NMR (DMSO-d$_6$, δ): 1.37 (3H, t, J=6.9 Hz), 3.89 (2H, s), 4.52 (2H, q, J=6.9 Hz), 5.10 (2H, s), 7.2–7.4 (5H, m), 8.73 (1H, s)

Preparation 13-1)

The following compound was obtained according to a similar manner to that of Preparation 15-6) by using ethoxycarbonylmethyl bromide.

6-Cyano-1-ethoxycarbonylmethyl-2,3-dihydro-2-oxo-1H-thieno[2,3-b][1,4]thiazine

IR (Nujol): 2210, 1725, 1675 cm$^{-1}$
MASS (z/e): 283 (M+H)$^+$
NMR (DMSO-d$_6$, δ): 1.20 (3H, t, J=7.1 Hz), 3.79 (2H, s), 4.13 (2H, q, J=7.1 Hz), 4.64 (2H, s), 7.98 (1H, s)

Preparation 13-2)

The following compound was obtained according to a similar manner to that of Preparation 5-2).

6-(1-Ethoxy-1-iminomethyl)-1-ethoxycarbonylmethyl-2,3-dihydro-2-oxo-1H-thieno[2,3-b][1,4]thiazine hydrochloride IR (Nujol): 1760, 1690, 1600 cm$^{-1}$
(+) APCI MASS: 329 (M+H)$^+$
NMR (DMSO-d$_6$, δ): 1.22 (3H, t, J=7.1 Hz), 1.41 (3H, t, j=7.0 Hz), 3.84 (2H, s), 4.16 (2H, q, J=7.1 Hz), 4.5–4.7 (4H, m), 8.58 (1H, s)

Preparation 14

The following compound was obtained according to a similar manner to that of Preparation 5-2).

2,3-Dihydro-2-oxo-1H-thieno[2,3-b][1,4]thiazine hydrochloride (+) APCI MASS: 243 (M+H)$^+$ Preparation 15-1)

The following compound was obtained according to a similar manner to that of Preparation 15-6) by using 2-oxo-1,3-dioxolane.

6-Cyano-2,3-dihydro-1-(2-hydroxyethyl)-2-oxo-1H-thieno[2,3-b][1,4]thiazine (+) APCI MASS: 241 (M+H)$^+$ NMR (DMSO-d$_6$, δ): 3.4–3.6 (2H, m), 3.71 (2H, s), 3.8–4.0 (2H, m), 4.83 (1H, t, J=5.5 Hz), 8.01 (1H, s)

Preparation 15-2)

The following compound was obtained according to a similar manner to that of Preparation 15-6) by using n-butylcarbamoylmethyl bromide.

1-(n-Butylcarbamoylmethyl)-6-cyano-2,3-dihydro-2-oxo-1H-thieno[2,3-b][1,4]thiazine (+) APCI MASS: 310 (M+H)$^+$ NMR (DMSO-d$_6$, δ): 0.8–1.0 (3H, m), 1.1–1.5 (4H, m), 3.0–3.2 (2H, m), 3.76 (2H, s), 4.44 (2H, s), 7.78 (1H, s), 8.06 (1H, t, J=5.4 Hz)

Preparation 15-3)

The following compound was obtained according to a similar manner to that of Preparation 15-6) by using 2,2,2-trifluoroethylcarbamoylmethyl bromide.

6-Cyano-1-(2,2,2-trifluoroethylcarbamoylmethyl)-2,3-dihydro-2-oxo-1H-thieno[2,3-b][1,4]thiazine IR (Nujol): 3300, 3100, 2220, 1670, 1580 cm$^{-1}$ NMR (DMSO-d$_6$, δ): 3.77 (2H, s), 3.8–4.1 (2H, m), 4.56 (2H, s), 7.80 (1H, s), 8.84 (1H, t, J=6.2 Hz)

Preparation 15-4)

The following compound was obtained according to a similar manner to that of Preparation 15-6) by using 3-ethoxycarbonylpropyl bromide.

6-Cyano-1-(3-ethoxycarbonylpropyl)-2,3-dihydro-2-oxo-1H-thieno[2,3-b][1,4]thiazine (+) APCI MASS: 311 (M+H)$^+$ NMR (DMSO-d$_6$, δ): 1.18 (3H, t, J=7.1 Hz), 1.6–1.9 (2H, m), 2.32 (2H, t, J=7.3 Hz), 3.72 (2H, s), 3.8–3.9 (2H, m), 4.05 (2H, q, J=7.1 Hz), 8.06 (1H, s)

Preparation 15-5)

The following compound was obtained according to a similar manner to that of Preparation 15-6) by using 3,4-methylenedioxyphenylcarbamoylmethyl bromide.

6-Cyano-2,3-dihydro-1-(3,4-methylenedioxyphenylcarbamoylmethyl)-2-oxo-1H-thieno[2,3-b][1,4]thiazine IR (Nujol): 2210, 1670, 1540 cm$^{-1}$ (+) APCI MASS: 374 (M+H)$^+$ NMR (DMSO-d$_6$, δ): 3.79 (2H, s), 4.64 (2H, s), 5.98 (2H, s), 6.86 (1H, d, J=8.4 Hz), 6.95 (1H, dd, J=1.9, 8.4 Hz), 7.28 (1H, d, J=1.9 Hz), 7.95 (1H, s), 10.18 (1H, s)

Preparation 15-6)

To a solution of 6-cyano-2,3-dihydro-2-oxo-1H-thieno[2,3-b][1,4]thiazine (13.6 g) in N,N-dimethylformamide (270 ml) was added potassium tert-butoxide (9.3 g) under ice cooling. After stirring for 10 minutes under ice cooling, to the reaction mixture was added 1-iodobutane (9.5 ml). After stirring for 8 hours at room temperature, the reaction mixture was poured into a mixture of ethyl acetate and water. The organic layer was successively washed with water and brine and dried over magnesium sulfate. The solvent was evaporated in vacuo and the residue was purified by column chromatography on silica gel eluting with chloroform. The fractions containing the object compounds were collected and evaporated in vacuo to give 1-n-butyl-6-cyano-2,3-dihydro-2-oxo-1H-thieno[2,3-b][1,4]thiazine (13.78 g).

IR (Nujol): 2200, 1660, 1540 cm$^{-1}$ (+) APCI MASS: 253 (M+H)$^+$

NMR (DMSO-d$_6$, δ): 0.87 (3H, t, J=7.2 Hz), 1.2–1.6 (4H, m), 3.71 (2H, s), 3.8–3.9 (2H, m), 8.07 (1H, s)

The following compounds were obtained according to a similar manner to that of Preparation 5-2).

Preparation 16-1)

2,3-Dihydro-6-(1-ethoxy-1-iminomethyl)-1-(2-hydroxyethyl)-2-oxo-1H-thieno[2,3-b][1,4]thiazine hydrochloride, which was used in the next reaction without further purification.

Preparation 16-2)

1-(n-Butylcarbamoylmethyl)-2,3-dihydro-6-(1-ethoxy-1-iminomethyl)-2-oxo-1H-thieno[2,3-b][1,4]thiazine hydrochloride (+) APCI MASS: 356 (M+H)$^+$ NMR (DMSO-d$_6$, δ): 0.8–0.9 (3H, m), 1.2–1.5 (7H, m), 3.0–3.2 (2H, m), 3.81 (2H, s), 4.42 (2H, s), 4.57 (2H, q, J=6.9 Hz), 8.20 (1H, t, J=5.5 Hz), 8.38 (1H, s)

Preparation 16-3)

1-(2,2,2-Trifluoroethylcarbamoylmethyl)-2,3-dihydro-6-(1-ethoxy-1-iminomethyl)-2-oxo-1H-thieno[2,3-b][1,4]thiazine hydrochloride IR (Nujol): 3250, 1705, 1675, 1590, 1550 cm$^{-1}$ (+) APCI MASS: 382 (M+H)$^+$ NMR (DMSO-d$_6$, δ): 1.41 (3H, t, J=7.0 Hz), 3.4–4.1 (4H, m), 4.4–4.7 (4H, m), 8.40 (1H, s), 8.8–9.1 (1H, m)

Preparation 16-4)

1-(3-Ethoxycarbonylpropyl)-2,3-dihydro-6-(1-ethoxy-1-iminomethyl)-2-oxo-1H-thieno[2,3-b][1,4]thiazine hydrochloride (+) APCI MASS: 357 (M+H)$^+$ NMR (DMSO-d$_6$, δ): 1.17 (3H, t, J=7.1 Hz), 1.41 (3H, t, J=6.9 Hz), 1.7–1.9 (2H, m), 2.37 (2H, t, J=7.5 Hz), 3.77 (2H, s), 3.89 (2H, t, J=7.1 Hz), 4.04 (2H, q, J=7.1 Hz), 4.57 (2H, q, J=6.9 Hz), 8.83 (1H, s)

Preparation 16-5)

2,3-Dihydro-6-(1-ethoxy-1-iminomethyl)-1-(3,4-methylenedioxyphenylcarbamoylmethyl)-2-oxo-1H-thieno[2,3-b][1,4]thiazine hydrochloride (+) APCI MASS: 420 (M+H)$^+$ NMR (DMSO-d$_6$, δ): 1.41 (3H, t, J=7.1 Hz), 3.84 (2H, s), 4.5–4.7 (4H, m), 5.98 (2H, s), 6.86 (1H, d, J=8.4 Hz), 7.00 (1H, dd, J=2.0, 8.4 Hz), 7.2–7.4 (1H, m), 8.50 (1H, s), 10.44 (1H, s)

Preparation 16-6)

1-n-Butyl-2,3-dihydro-6-(1-ethoxy-1-iminomethyl)-2-oxo-1H-thieno[2,3-b][1,4]thiazine hydrochloride IR (Nujol): 1680, 1605 cm$^{-1}$ (+) APCI MASS: 299 (M+H)$^+$ NMR (DMSO-d$_6$, δ): 0.89 (3H, t, j=7.2 Hz), 1.2–1.6 (7H, m), 3.75 (2H, s), 3.8–3.9 (2H, m), 4.58 (2H, q, J=7.0 Hz), 8.82 (1H, s)

Preparation 17

Under nitrogen atmosphere, potassium hydroxide (147 mg) in dimethyl sulfoxide (10 ml) was stirred at room temperature for 30 minutes. To the solution were added 2,3-dihydro-6-methoxycarbonyl-2-oxothieno[2,3-b][1,4]thiazine (0.50 g), sodium iodide (0.39 g) and 2-chloroethyl methyl sulfide (0.26 ml), and the mixture was stirred at 50° C. for 6.5 hours. The mixture was poured into water and extracted with ethyl acetate. The organic layer was washed with water and brine, dried over anhydrous sodium sulfate and evaporated under reduced pressure. The residue was purified by column chromatography on silica gel (eluent:hexane:ethyl acetate=3:1) to give 2,3-dihydro-6-methoxycarbonyl-1-[2-(methylthio)-ethyl]-2-oxothieno[2,3-b][1,4]thiazine (465 mg).

NMR (DMSO-d$_6$, δ): 2.08 (3H, s), 2.62 (2H, t, J=7.2 Hz), 3.71 (2H, s), 4.10 (2H, t, J=6.9 Hz), 7.86 (1H, s)

Preparation 18-1)

Sodium borohydride (0.17 g) was added into a mixture of 6-ethoxycarbonyl-4,5,6-7-tetrahydro-4-oxobenzo[b]thiophene (1.00 g) and methanol (MeOH) (20 ml) in a portion at room temperature (r.t.) under nitrogen atmosphere, and the mixture was stirred at room temperature for 30 minutes. The reaction mixture was added into a mixture of ethyl acetate (AcOEt) and water, and was adjusted to pH 1.6 with 6 N hydrochloric acid (HCl). The separated organic layer was washed with a saturated aqueous solution of sodium hydrogen carbonate (sat. NaHCO$_3$ aq.), water, and brine, and dried over magnesium sulfate (MgSO$_4$), and then evaporated in vacuo. After evaporation of the filtrate, the resulting oil was purified by chromatography on silica gel (chloroform (CHCl$_3$)-MeOH as eluent) to give 6-ethoxycarbonyl-4-hydroxy-4,5,6,7-tetrahydrobenzo[b]thiophene (0.79 g) as an oil.

IR (KBr): 3433, 1730 cm$^{-1}$

APCI MASS: 225 (M−H)

NMR (CDCl$_3$, δ): 1.27 (3H, t, J=7.1 Hz), 1.96 (2H, m), 2.18 (2H, m), 2.99 (1H, m), 4.22 (2H, q, J=7.1 Hz), 6.1 (1H, t J=6.1 Hz), 7.06 (1H, d, J=5.2 Hz), 7.12 (1H, d, J=5.2 Hz)

Process 18-2)

Acetic anhydride (4.1 ml) was added to a mixture of 6-ethoxycarbonyl-4-hydroxy-4,5,6,7-tetrahydrobenzo[b]thiophene (2.06 g) and pyridine (8 ml) under water cooling, and was stirred at r.t. for 2.5 hours. The reaction mixture was added into a mixture of AcOEt and water, and was adjusted to pH 1.6 with 6N HCl. The separated organic layer was washed with a saturated aqueous solution of sodium hydrogen carbonate (sat. NaHCO$_3$ aq.), water, and brine, and dried over MgSO$_4$, and then evaporated in vacuo to give 4-acetoxy-6-ethoxycarbonyl-4,5,6,7-tetrahydrobenzo[b]thiophene (2.36 g) as an oil.

APCI MASS: 269 (M+H)

NMR (CDCl$_3$, δ): 1.29 (3H, t, J=7.1 Hz), 2.09 (3H, s), 1.9–2.6 (2H, m), 2.95–3.2 (3H, m), 4.22 (2H, q, J=7.1 Hz), 6.05 (1H, m), 6.82 (1H, d, J=5.2 Hz), 7.10 (1H, d, J=5.2 Hz)

Preparation 18-3)

A mixture of 4-acetoxy-6-ethoxycarbonyl-4,5,6,7-tetrahydrobenzo[b]thiophene (2.34 g), tosic acid monohydrate (0.13 g), and toluene (50 ml) was stirred at reflux for 2 hours. A saturated aqueous solution of sodium hydrogen carbonate was added to the reaction mixture, and then the separated organic layer was washed with a saturated aqueous solution of sodium hydrogen carbonate, water, and brine, and dried over MgSO$_4$, and then evaporated in vacuo. After evaporation of the filtrate, the resulting oil was purified by chromatography on silica gel (CHCl$_3$-MeOH as eluent) to give 6-ethoxycarbonyl-6,7-dihydrobenzo[b]thiophene (1.03 g) as an oil.

APCI MASS: 209 (M+H)

NMR (CDCl$_3$, δ): 1.30 (3H, t, J=7.1 Hz), 3.10 and 3.13 (2H, each s), 3.4–3.7 (1H, m), 4.15 (2H, q, J=7.1 Hz), 5.90 (1H, dd, J=9.6, 3.4 Hz), 6.53 (1H, dd, J=9.6, 3.4 Hz), 6.83 (1H, d, J=5.1 Hz), 7.03 (1H, d, J=5.1 Hz)

Preparation 18-4)

A mixture of 6-ethoxycarbonyl-6,7-dihydrobenzo[b]thiophene (1.00 g), 10% palladium on carbon (2.16 g), AcOEt (30 ml) and MeOH (10 ml) was stirred at r.t. under hydrogen atmosphere for 4 hours. After removal of insoluble solids, the filtrate was concentrated in vacuo to give 6-ethoxycarbonyl-4,5,6,7-tetrahydrobenzo[b]thiophene (0.96 g) as an oil.

IR (Neat): 2935, 1730, 1596 cm$^{-1}$

APCI MASS: 211 (M+H)

NMR (CDCl$_3$, δ): 1.28 (3H, t, J=7.1 Hz), 1.6–2.4 (3H, m), 2.6–3.3 (4H, m), 4.14 (2H, q, J=7.1 Hz), 6.75 (1H, d, J=5.1 Hz), 7.07 (1H, d, J=5.1 Hz)

Preparation 18-5)

A mixture of 6-ethoxycarbonyl-4,5,6,7-tetrahydrobenzo[b]thiophene (0.80 g) and dichloromethane (CH$_2$Cl$_2$) was dropwise added to a mixture of aluminum chloride (AlCl$_3$) (1.01 g) and CH$_2$Cl$_2$ (5 ml) under ice-water cooling, and was stirred under the same conditions for 15 minutes. A mixture of 1,1-dichloromethyl methyl ether (0.52 ml) and CH$_2$Cl$_2$ (3 ml) was thereto added, and was stirred under the same conditions for 10 minutes. The reaction mixture was added into a mixture of CHCl$_3$, ice, and water. The separated organic layer was washed with water, and brine, and dried over MgSO$_4$. After evaporation of the filtrate, the resulting oil was purified by chromatography on silica gel (n-hexane-AcOEt as eluent) to give 6-ethoxycarbonyl-2-formyl-4,5,6,7-tetrahydrobenzo[b]thiophene (0.33 g).

IR (Neat): 2935, 1730, 1596 cm$^{-1}$

APCI MASS: 239 (M+H)

NMR (CDCl$_3$, δ): 1.26 (3H, t, J=7.1 Hz), 1.6–2.4 (3H, m), 2.6–3.3 (4H, m), 4.16 (2H, q, J=7.1 Hz), 7.43 (1H, s), 9.80 (1H, s)

Preparation 18-6)

A mixture of 6-ethoxycarbonyl-2-formyl-4,5,6,7-tetrahydrobenzo[b]thiophene (3.23 g), hydroxylamine hydrochloride (0.92 g), and ethanol (EtOH) (30 ml) was stirred at reflux for 30 minutes. The reaction mixture was added into a mixture of AcOEt and water. The separated organic layer was washed with water, and brine, and dried over MgSO$_4$. After evaporation of the filtrate, the resulting precipitate was washed with a mixture of n-hexane and isopropyl ether to give 6-ethoxycarbonyl-2-hydroxyimino-4,5,6,7-tetrahydrobenzo[b]thiophene (1.81 g).

APCI MASS: 254 (M+H)

NMR (DMSO-d$_6$, δ): 1.26 (3H, t, J=7.1 Hz), 1.6–3.2 (7H, m), 4.14 (2H, q, J=7.1 Hz), 7.11 (1H, s), 7.67 (1H, s)

Preparation 18-7)

A mixture of 6-ethoxycarbonyl-2-hydroxyimino-4,5,6,7-tetrahydrobenzo[b]thiophene (1.77 g) and acetic anhydride (0.84 ml) was stirred at reflux for 45 minutes. The reaction mixture was added into a mixture of AcOEt and water. The separated organic layer was washed with water, and brine, and dried over MgSO$_4$. After evaporation of the filtrate, the resulting precipitate was washed with n-hexane to give 6-ethoxycarbonyl-2-cyano-4,5,6,7-tetrahydrobenzo[b] thiophene (1.28 g).

IR (Neat): 2937, 2212, 1724 cm$^{-1}$
APCI MASS: 236 (M+H)
NMR (DMSO-d$_6$, δ): 1.26 (3H, t, J=7.1 Hz), 1.6–3.2 (7H, m), 4.14 (2H, q, J=7.1 Hz), 7.66 (1H, s)

Preparation 18-8)

A mixture of 6-ethoxycarbonyl-2-cyano-4,5,6,7-tetrahydrobenzo[b]thiophene (1.26 g), and EtOH (10 ml) was bubbled with hydrogen chloride with ice-water cooling. After being saturated with hydrogen chloride, the mixture was stirred at r.t. for 3 hours. The reaction mixture was evaporated to give precipitate. The resulting precipitate was washed with diethyl ether (Et$_2$O) to give 6-ethoxycarbonyl 2-(1-ethoxy-1-iminomethyl)-4,5,6,7-tetrahydrobenzo[b] thiophene hydrochloride (1.55 g).

NMR (DMSO-d$_6$, δ): 1.16 (3H, t, J=7.1 Hz), 1.26 (3H, t, J=7.1 Hz), 1.6–3.2 (7H, m), 4.11 (2H, q, J=7.1 Hz), 4.58 (2H, q, J=7.1 Hz), 8.22 (1H, s)

Preparation 19-1)

The following compound was obtained according to a similar manner to that of Preparation 20-1).

2-(Methoxycarbonylmethylthio)-5-cyano-3-nitrothiophene

NMR (DMSO-d$_6$, δ): 3.75 (3H, s), 4.37 (2H, s), 8.61 (1H, s)

Preparation 19-2)

The following compound was obtained according to a similar manner to that of Preparation 20-2).

6-Cyano-2,3-dihydro-2-oxothieno[2,3-b][1,4] thiazine

NMR (DMSO-d$_6$, δ) 3.64 (2H, s), 7.45 (1H, s), 10.85 (1H, s)

Preparation 20-1)

To a mixture of 2-bromo-5-methoxycarbonyl-3-nitrothiophene (110.7 g) and methyl mercaptoacetate (37.2 ml) in tetrahydrofuran (1 l) was added triethylamine (63.8 ml). After stirring for 4 hours at room temperature, the reaction mixture was poured into water. The resulting precipitate was collected by filtration and washed with water to give 2-methoxycarbonylmethylthio-5-methoxycarbonyl-3-nitrothiophene (118.15 g).

NMR (DMSO-d$_6$, δ): 3.74 (3H, s), 3.86 (3H, s), 4.37 (2H, s), 8.16 (1H, s)

Preparation 20-2)

To a solution of 2-methoxycarbonylmethylthio-5-methoxycarbonyl-3-nitrothiophene (26.1 g) in acetic acid (360 ml) and water (36 ml) was added portionwise iron (36.5 g) at 80° C. After stirring for 3 hours at 80° C., the hot reaction mixture was filtered and the filtrate was poured into ice-water. The resulting precipitate was collected by filtration and washed with water to give 2,3-dihydro-6-methoxycarbonyl-2-oxothieno[2,3-b][1,4] thiazine (11.12 g).

NMR (DMSO-d$_6$, δ): 3.63 (2H, s), 3.80 (3H, s), 7.31 (1H, s)

Preparation 21-1)

The following compound was obtained according to a similar manner to that of Preparation 6-2).

6-Cyano-2,3-dihydrothieno[2,3-b][1,4] thiazine

NMR (DMSO-d$_6$, δ): 3.0–3.1 (2H, m), 3.4–3.6 (2H, m), 6.0–6.2 (1H, m), 7.23 (1H, s)

Preparation 21-2)

The following compound was obtained according to a similar manner to that of Preparation 23-1).

6-Cyano-2,3-dihydro-1-(ethoxycarbonylacetyl) thieno [2,3-b][1,4] thiazine

IR (Nujol): 2220, 1740, 1660 cm$^{-1}$
(+) APCI MASS: 297 (M+H)$^+$
NMR (DMSO-d$_6$, δ): 1.0–1.3 (3H, m), 3.2–3.5 (2H, m), 3.80 (2H, s), 3.9–4.3 (4H, m), 8.19 (1H, s)

Preparation 21-3)

The following compound was obtained according to a similar manner to that of Preparation 5-2).

Ethyl 2,3-dihydro-1-(ethoxycarbonylacetyl)-6-(1-ethoxy-1-iminomethyl)thieno[2,3-b][1,4] thiazine hydrochloride (+) APCI MASS: 343 (M+H)$^+$
NMR (DMSO-d$_6$, δ): 1.1–1.5 (6H, m), 3.3–4.2 (8H, m), 4.58 (2H, q, J=7.0Hz), 8.80 (1H, s)

Preparation 22-1)

The following compound was obtained according to a similar manner to that of Preparation 6-2).

2,3-Dihydro-6-methoxycarbonylthieno[2,3-b][1,4] thiazine

IR (Nujol): 3350, 1680, 1565 cm$^{-1}$
(+) APCI MASS: 216 (M+H)$^+$
NMR (DMSO-d$_6$, δ): 3.0–3.1 (2H, m), 3.4–3.5 (2H, m), 3.75 (3H, s), 5.9–6.0 (1H, m), 7.13 (1H, s)

Preparation 22-2)

The following compound was obtained according to a similar manner to that of Preparation 23-1).

1-Benzoyl-2,3-dihydro-6-methoxycarbonylthieno[2, 3-b][1, 4] thiazine

IR (Nujol): 1690, 1640 cm$^{-1}$
(+) APCI MASS: 320 (M+H)$^+$
NMR (DMSO-d$_6$, δ): 3.3–3.4 (2H, m), 3.76 (3H, s), 3.9–4.1 (2H, m), 7.4–7.8 (6H, m)

Preparation 22-3)

The following compound was obtained according to a similar manner to that of Preparation 3-3).

1-Benzoyl-6-carboxy-2,3-dihydrothieno[2,3-b][1,4] thiazine

IR (Nujol): 1635 cm$^{-1}$
(+) APCI MASS: 306 (M+H)$^+$
NMR (DMSO-d$_6$, δ): 3.2–3.4 (2H, m), 3.9–4.1 (2H, m), 7.4–7.6 (6H, m), 13.05 (1H, s)

Preparation 22-4)

The following compound was obtained according to a similar manner to that of Preparation 3-7).

1-Benzoyl-6-carbamoyl-2,3-dihydrothieno[2,3-b][1, 4] thiazine

IR (Nujol): 1660, 1620 cm$^{-1}$
(+) APCI MASS: 305 (M+H)$^+$
NMR (DMSO-d$_6$, δ): 3.3–3.4 (2H, m), 3.9–4.0 (2H, m), 7.28 (1H, br s), 7.4–7.6 (5H, m), 7.7–8.0 (2H, m)

Preparation 22-5)

The following compound was obtained according to a similar manner to that of Preparation 11-5).

1-Benzoyl-6-cyano-2,3-dihydrothieno[2,3-b][1,4]thiazine

IR (Nujol): 2220, 1640 cm$^{-1}$ (+) APCI MASS: 287 (M+H)$^+$

NMR (DMSO-d$_6$, δ): 3.3–3.4 (2H, m), 3.9–4.1 (2H, m), 7.4–7.6 (5H, m), 7.80 (1H, s)

Preparation 22-6)

The following compound was obtained according to a similar manner to that of Preparation 5-2).

1-Benzoyl-6-(1-ethoxy-1-iminomethyl)-2,3-dihydrothieno [2,3-b][1,4] thiazine hydrochloride (+) APCI MASS: 333 (M+H)$^+$ NMR (DMSO-d$_6$, δ): 1.3–1.5 (3H, m), 3.3–3.5 (2H, m), 3.9–4.0 (2H, m), 4.56 (2H, q, J=7.0Hz), 7.4–7.6 (5H, m), 8.53 (1H, s)

Preparation 23-1)

To a mixture of 6-cyano-2,3-dihydrothieno[2,3-b][1,4]thiazine (0.3 g) and triethylamine (0.46 ml) in dichloromethane (10 ml) was dropwise added acetyl chloride (0.23 ml). After stirring for 5 hours at room temperature, the reaction mixture was poured into a mixture of ethyl acetate and water. The organic layer was successively washed with brine and dried over magnesium sulfate. The solvent was evaporated in vacuo and the residue was pulverized from diisopropyl ether to give 1-acetyl-6-cyano-2,3-dihydrothieno [2,3-b][1,4] thiazine (0.33 g)

IR (Nujol): 2200, 1660 cm$^{-1}$

NMR (DMSO-d$_6$, δ): 2.21 (3H, s), 3.2–3.4 (2H, m), 3.9–4.0 (2H, m), 8.18 (1H, s)

Preparation 23-2)

The following compound was obtained according to a similar manner to that of Preparation 5-2).

1-Acetyl-6-(1-ethoxy-1-iminomethyl)-2,3-dihydrothieno [2,3-b][1,4] thiazine hydrochloride IR (Nujol): 1665, 1595 cm$^{-1}$ (+) APCI MASS: 271 (M+H)$^+$ NMR (DMSO-d$_6$, δ): 1.3–1.5 (3H, m), 2.26 (3H, s), 3.2–3.5 (2H, m), 3.9–4.1 (2H, m), 4.5–4.7 (2H, m), 8.81 (1H, s)

Preparation 24-1)

The following compound was obtained according to a similar manner to that of Preparation 15-6).

2,3-Dihydro-1-ethyl-6-methoxycarbonyl-2-oxothieno [2,3-b][1,4] thiazine

IR (Nujol): 1700, 1650 cm$^{-1}$

NMR (DMSO-d$_6$, δ): 1.08 (3H, t, J=7.1Hz), 3.69 (2H, s), 3.83 (3H, s), 3.92 (2H, q, J=7.1 Hz), 7.77 (1H, s)

Preparation 24-2)

The following compound was obtained according to a similar manner to that of Preparation 6-2).

2,3-Dihydro-1-ethyl-6-methoxycarbonylthieno[2,3-b][1,4] thiazine

IR (Nujol): 2950, 1700, 1550 cm$^{-1}$ (+) APCI MASS: 244 (M+H)$^+$

NMR (DMSO-d$_6$, δ): 1.02 (3H, t, J=7.0Hz), 3.1–3.5 (6H, m), 3.76 (3H, s), 7.41 (1H, s)

EXAMPLE 1

To a mixture of ammonium chloride (NH$_4$Cl) (66.5 mg) and toluene (3 ml) was dropwise added 2 M trimethylalminum (AlMe$_3$) (0.62 ml) under nitrogen atmosphere at r.t., and the mixture was stirred at r.t. for 1 hour. To the reaction mixture was added a mixture of 4-(N-butylcarbamoylmethylidene)-2-methoxycarbonyl-4,5,6,7-tetrahydrobenzo[b]thiophene (95.6 mg) and toluene (2 ml). The reaction mixture was stirred at reflux for 8 hours. After being allowed to cool at room temperature, the reaction mixture was poured into a mixture of chloroform (CHCl$_3$) and MeOH. After removal of insoluble solids, the filtrate was evaporated in vacuo. The resulting residue was purified by chromatography on silica gel (CHCl$_3$-MeOH as an eluent). The fractions including the object compound were collected and evaporated in vacuo. The resulting precipitate was washed with Et$_2$O to give 4-(N-butylcarbamoylmethylidene)-2-amidino-4,5,6,7-tetrahydrobenzo[b] thiophene (39.8 mg).

mp: 114–117° C.

IR (KBr): 3274, 1648, 1558, 1540, 1508 cm$^{-1}$

MASS (z/e): 292 (M+H)$^+$of free

NMR (DMSO-d$_6$, δ): 0.88 (2H, t, J=6.9Hz), 1.2–1.6 (4H, m), 1.87 (2H, m), 2.94 (2H, t, J=5.6Hz), 3.0–3.2 (4H, m), 6.30 (1H, s), 8.05 (1H, t, J=7.5Hz), 8.37 (1H, s), 9.31 (4H, s)

EXAMPLE 2-1)

The following compound was obtained according to a similar manner to that of Example 1.

2-Amidino-4-n-butylidene-4,5,6,7-tetrahydrobenzo[b]thiophene hydrochloride mp: 115–118° C.

IR (KBr): 3085, 1660, 1564, 1504 cm$^{-1}$

MASS (z/e): 235 (M+H)$^+$of free

NMR (DMSO-d$_6$, δ): 0.88 (3H, m), 1.3–3.0 (10H, m), 5.67 and 5.95 (1H, each t, J=7.2 Hz), 8.10 and 8.39 (1H, each s), 9.14 and 9.32 (4H, each s)

EXAMPLE 2-2)

The following compound was obtained according to a similar manner to that of Example 4-2).

2-Amidino-4-n-butyl-4,5,6,7-tetrahydrobenzo[b]thiophene trifluoroacetate mp : 235–238° C.

IR (KBr): 3305, 3093, 2937, 1668, 1597, 1512 cm$^{-1}$

MASS (z/e): 237 (M+H)$^+$of free

NMR (DMSO-d$_6$, δ): 0.91 (3H, m), 1.2–3.0 (13H, m), 7.91 (1H, s), 9.01 and 9.10 (4H, each s)

EXAMPLE 3

A mixture of 4-n-butylidene-2-(1-ethoxy-1-iminomethyl)-5,6,7,8-tetrahydro-4H-cyclohepta[b]thiophene hydrochloride (0.34 g), 2.7 N ethanol solution of ammonia (1.00 ml) and EtOH (20 ml) was stirred at reflux for 6 hours. After evaporation, the resulting oil was purified by chromatography on silica gel (CHCl$_3$-MeOH as an eluent). The fractions including the object compound were collected and evaporated in vacuo. The resulting syrup was dissolved with a mixture of 0.1% TFA aqueous solution and acetonitrile (CH$_3$CN), and lyophilized to give 2-amidino-4-n-butylidene-5,6,7,8-tetrahydro-4H-cyclohepta[b]thiophene trifluoroacetate (84.2 mg).

mp: 91–94° C.

IR (KBr): 3087, 1660, 1564, 1504 cm$^{-1}$

MASS (z/e): 249 (M+H)$^+$ of free

NMR (DMSO-d$_6$, δ): 0.7–2.4 (13H, m), 2.89 (2H, t, j=6.1Hz), 5.71 and 5.89 (1H, each t, J=7.4 Hz (at 5.71) and 5.8 (at 5.89)), 8.00 and 8.12 (1H, each s), 9.11, 9.26, and 9.33 (4H, each s)

EXAMPLE 4-1)

The following compound was obtained according to a similar manner to that of Example 1.

2-Amidino-4-n-butylidene-4,5,6,7-tetrahydrobenzo [b]furan hydrochloride mp: 156–160° C.

IR (KBr): 3336, 3101, 1672, 1612, 1556 cm$^{-1}$

MASS (z/e): 219 (M+H)$^+$ of free

NMR (DMSO-d$_6$, δ): 0.90 (3H, t, J=7.4Hz), 1.38 (2H, q, J=7.4 Hz), 1.90 (2H, m), 2.14 (2H, q, J=7.4 Hz), 2.38 (2H, m), 2.78 (2H, t, J=6.3 Hz), 5.36 and 5.63 (1H, each t, J=7.4 Hz), 8.06 (1H, s), 9.12 and 9.37 (4H, each br s)

EXAMPLE 4-2)

A mixture of 2-amidino-4-n-butylidene-4,5,6,7-tetrahydrobenzo[b]furan hydrochloride (107.3 mg), 10% Pd on carbon, and MeOH (1 ml) was stirred at r.t. under hydrogen (H$_2$) atmosphere for 2 hours. After removal of the catalyst, the filtrate was evaporated, and dissolved in a mixture of acetonitrile (CH$_3$CN) and 0.1% aqueous trifluoroacetic acid (TFA aq). The solution was subjected to preparative High Performance Liquid Chromatography (HPLC) under the following condition:

Preparative HPLC condition:

Column: YMC-PACK-ODS-15 S-15 120A 50φ×250 mm

Eluent: 40% CH$_3$CN in 0.1% TFA aq

Flow: 118 ml/minutes

Fractions including the object compound were combined, concentrated in vacuo, and lyophilized to give 2-amidino-4-butyl-4,5,6,7-tetrahydrobenzo[b] furan (0.05 g).

mp: 243–245° C.

IR (KBr): 3305, 3104, 2937, 1672, 1569 cm$^{-1}$

MASS (z/e): 221 (M+H)$^+$ of free

NMR (DMSO-d$_6$, δ): 0.90 (3H, m), 1.2–2.2 (11H, m), 2.80 (2H, m), 7.65 (1H, s), 8.88 and 9.09 (4H, each s)

EXAMPLE 5

The following compound was obtained according to a similar manner to that of Example 3.

6-Amidino-1-butyl-2,3-dihydro-2-oxo-1H-thieno[2, 3-b][1,4] thiazine 4,4-dioxide hydrochloride IR (Nujol): 1670, 1550, 1510 cm$^{-1}$ (+) APCI MASS: 302 (M+H)$^+$ NMR (DMSO-d$_6$, δ): 0.89 (3H, t, J=7.2Hz), 1.2–1.7 (4H, m), 3.9–4.1 (2H, m), 5.05 (2H, s), 8.37 (1H, s), 9.50 (4H, br s)

Elemental Analysis for C$_{11}$H$_{16}$ClN$_3$O$_3$S$_2$.1.6H$_2$O Calcd.: C, 36.03; H, 5.28; N, 11.46. Found: C, 36.01; H, 5.07; N, 11.30.

EXAMPLE 6

The following compound was obtained according to a similar manner to that of Example 1.

6-Amidino-1-butyl-2,3-dihydro-1H-thieno[2,3-b][1, 4] thiazine trifluoroacetate

IR (Nujol): 1655, 1570, 1505 cm$^{-1}$ (+) APCI MASS: 256 (M+H)$^+$

NMR (DMSO-d$_6$, δ): 0.92 (3H, t, J=7.2Hz), 1.2–1.6 (4H, m), 3.1–3.3 (4H, m), 3.4–3,6 (2H, m), 7.73 (1H, s), 9,01 (4H, br s)

EXAMPLE 7

The following compound was obtained according to a similar manner to that of Example 1.

6-Amidino-1-benzyl-2,3-dihydro -1H-thieno[2,3-b] [1,4] thiazine hydrochloride

IR (Nujol): b 1650, 1570, 1500 cm $^{-1}$ (+) APCI MASS: 290 (M+H)$^+$

NMR (DMSO-d$_6$, δ): 3.0–3.2 (2H, m) 3.4–3.6 (2H, m), 4.4–4.6 (2H, m), 7.2–7.5 (5H, m), 8.07 (1H, s), 9.06 (4H, br s)

The following compounds were obtained according to a similar manner to that of Example 3.

EXAMPLE 8-1)

6-Amidino-2,3-dihydro-1-(3,4-dimethoxyphenethyl)-2-oxo-1H-thieno[2,3-b][1,4] thiazine hydrochloride mp: 133–135° C.

IR (Nujol): 1660, 1565, 1505 cm$^{-1}$ (+) APCI MASS: 378 (M+H)$^+$

NMR (DMSO-d$_6$, δ): 2.7–2.9 (2H, m), 3.69 (3H, s), 3.72 (2H, s), 3.74 (3H, s), 4.0–4.2 (2H, m), 6,7–6.9 (3H, m), 8.29 (1H, s), 9.28 (4H, br s)

Elemental Analysis for C$_{17}$H$_{20}$ClN$_3$O$_3$S$_2$.1.2H$_2$O Calcd.: C, 46.88; H, 5.18; N, 9.65. Found: C, 46.60; H, 4.74; N 9.43.

EXAMPLE 8-2)

6-Amidino-1-cyclohexylmethyl-2,3-dihydro-2-oxo-1H-thieno[2,3-b][1,4] thiazine hydrochloride mp: >250° C.

IR (Nujol): 1665, 1565 cm$^{-1}$ (+) APCI MASS: 310 (M+H)$^+$

NMR (DMSO-d$_6$, δ) 0.8–1.2 (5H, m), 1.5–1.8 (6H, m), 3.7–3.8 (4H, m), 8.27 (1H, s), 9.30 (4H, br s)

Elemental Analysis for C$_{14}$H$_{20}$ClN$_3$OS$_2$. 1.3H$_2$O Calcd.: C 45.53, H 6.17, N 11.38. Found: C 45.51, H 6.14, N 11.14.

EXAMPLE 8-3)

6-Amidino-2,3-dihydro-2-oxo-1-phenethyl-1H-thieno [2,3-b][1,4]thiazine hydrochloride mp: >250° C.

IR (Nujol): 3350, 1675, 1630, 1570 cm$^{-1}$ (+) APCI MASS: 318 (M+H)$^+$

NMR (DMSO-d$_6$, δ): 2.8–3.0 (2H, m), 3.73 (2H, s), 4.0–4.2 (2H, m), 7.1–7.4 (5H, m), 8.27 (1H, s), 9.33 (4H, br s)

EXAMPLE 8-4)

6-Amidino-2,3-dihydro-1-(3,4-methylenedioxyphenethyl)-2-oxo-1H-thieno[2,3-b][1,4]thiazine hydrochloride mp: 161–162° C.

IR (Nujol): 1660, 1565, 1500 cm$^{-1}$ (+) APCI MASS: 362 (M+H)$^+$

NMR (DMSO-d$_6$, δ): 2.7–2.9 (2H, m), 3.72 (2H, s), 3.9–4.2 (2H, m), 5.96 (2H, s), 6.6–7.0 (3H, m), 8.25 (1H, s), 9.30 (4H, br s)

Elemental Analysis for $C_{16}H_{16}ClN_3O_3S_2 \cdot 1 \cdot OH_2O$ Calcd.: C 46.21, H 4.36, N 10.10. Found: C 46.03, H 4.02, N 9.69.

EXAMPLE 8-5)

6-Amidino-1-benzyl-2,3-dihydro-2-oxo-1H-thieno[2,3-b][1,4]thiazine hydrochloride mp: 164–166° C.

IR (Nujol): 1665, 1570 cm$^{-1}$ (+) APCI MASS: 304 (M+H)$^+$

NMR (DMSO-d$_6$, δ): 3.88 (2H, s), 5.10 (2H, s), 7.2–7.4 (5H, m), 8.26 (1H, s), 9.25 (4H, br s)

Elemental Analysis for $C_{14}H_{14}ClN_3OS_2 \cdot 1.2H_2O$ Calcd.: C 46.52, H 4.57, N 11.62. Found: C 46.52, H 4.18, N 11.58.

EXAMPLE 9-1)

The following compound was obtained according to a similar manner to that of Example 3.

6-Amidino-1-ethoxycarbonylmethyl-2,3-dihydro-2-oxo-1H-thieno[2,3-b][1,4]thiazine hydrochloride IR (Nujol): 3380, 1735, 1660, 1570 cm$^{-1}$ (+) APCI MASS: 300 (M+H)$^+$ NMR (DMSO-d$_6$, δ): 1.22 (3H, t, J=7.1Hz), 3.82 (2H, s), 4.16 (2H, q, J=7.1Hz), 4.63 (2H, s), 8.11 (1H, s), 9.24 (4H, br s)

EXAMPLE 9-2)

A mixture of 6-amidino-1-ethoxycarbonylmethyl-2,3-dihydro-2-oxo-1H-thieno[2,3-b][1,4]thiazine hydrochloride (0.15 g) and cHCl (1.5 ml) was stirred at 80° C. for 7 hours. The reaction mixture was evaporated in vacuo. The resulting oil was dissolved with water, and lyophilized to give 6-amidino-1-carboxymethyl-2,3-dihydro-2-oxo-1H-thieno[2,3-b]-[1,4]thiazine hydrochloride (90.6 mg).

IR (Nujol): 1715, 1665, 1575 cm$^{-1}$ (+) APCI MASS: 272 (M+H)$^+$

NMR (DMSO-d$_6$, δ): 3.81 (2H, s), 4.54 (2H, s), 8.09 (1H, s), 9.10 and 9.37 (4H, each s)

EXAMPLE 10

The following compound was obtained according to a similar manner to that of Example 3.

6-Amidino-2,3-dihydro-2-oxo-1H-thieno[2,3-b][1,4]thiazine hydrochloride mp: >250° C.

IR (Nujol): 3150, 1665 cm$^{-1}$ (+) APCI MASS: 214 (M+H)$^+$

NMR (DMSO-d$_6$, δ): 3.66 (2H, s), 7.72 (1H, s), 9.37 (4H, br s), 11.10 (1H, br s)

The following compounds were obtained according to a similar manner to that of Example 3.

EXAMPLE 11-1)

6-Amidino-2,3-dihydro-1-(2-hydroxyethyl)-2-oxo-1H-thieno[2,3-b][1,4]thiazine trifluoroacetate IR (Nujol): 1625 cm$^{-1}$ (+) APCI MASS: 258 (M+H)$^+$ NMR (DMSO-d$_6$, δ): 3.5–3.7 (2H, m), 3.74 (2H, s), 3.8–4.0 (2H, m), 8.09 (1H, s), 9.18 and 9.30 (4H, each s)

EXAMPLE 11-2)

6-Amidino-1-(n-butylcarbamoylmethyl)-2,3-dihydro-2-oxo-1H-thieno[2,3-b][1,4]thiazine hydrochloride IR (Nujol): 1650, 1560, 1500 cm$^{-1}$ NMR (DMSO-d$_6$, δ): 0.8–0.9 (3H, m), 1.2–1.5 (4H, m), 3.0–3.2 (2H, m), 3.79 (2H, s), 4.42 (2H, s), 8.03 (1H, s), 8.19 (1H, t, J=5.4 Hz), 9.23 (4H, br s)

EXAMPLE 11-3)

6-Amidino-1-(2,2,2-trifluoroethylcarbamoylmethyl)-2,3-dihydro-2-oxo-1H-thieno[2,3-b][1,4]thiazine hydrochloride IR (Nujol): 3300, 3100, 1640, 1570, 1510 cm$^{-1}$ (+) APCI MASS: 353 (M+H)$^+$ NMR (DMSO-d$_6$, δ): 3.80 (2H, s), 3.8–4.1 (2H, m), 4.53 (2H, s), 8.00 (1H, s), 8.9–9.1 (1H, m), 9.22 (4H, br s)

EXAMPLE 11-4)

2-Amidino-1-(3-ethoxycarbonylpropyl)-2,3-dihydro-2-oxo-1H-thieno[2,3-b][1,4]thiazine hydrochloride IR (Nujol): 3350, 1720, 1655, 1630, 1570 cm$^{-1}$ (+) APCI MASS: 328 (M+H)$^+$ NMR (DMSO-d$_6$, δ): 1.17 (3H, t, J=7.1 Hz), 1.7–1.9 (2H, m), 2.35 (2H, t, J=7.5 Hz), 3.75 (2H, s), 3.89 (2H, t, J=7.0 Hz), 4.04 (2H, q, J=7.1 Hz), 8.26 (1H, s), 9.29 (4H, br s)

EXAMPLE 11-5)

6-Amidino-2,3-dihydro-1-(3,4-methylenedioxyphenylcarbamoylmethyl)-2-oxo-1H-thieno[2,3-b][1,4]thiazine hydrochloride IR (Nujol): 1660, 1565 cm$^{-1}$ NMR (DMSO-d$_6$, δ): 3.82 (2H, s), 4.66 (2H, s), 5.98 (2H, s), 6.85 (1H, d, J=8.4 Hz), 7.02 (1H, d, J=8.4 Hz), 7.32 (1H, s), 8.19 (1H, s), 9.26 (4H, br s), 10.48 (1H, s)

---

Elemental Analysis for $C_{15}H_{16}ClN_3OS_2 \cdot 0.2H_2O$ Calcd.: C 50.40, H 4.62, N 11.75. Found: C 50.36, H 4.54, N 11.62.

EXAMPLE 11-6)

6-Amidino-1-n-butyl-2,3-dihydro-2-oxo-1H-thieno[2,3-b][1,4-]thiazine hydrochloride mp: 213–214° C.

IR (Nujol): 1640, 1570 cm$^{-1}$ (+) APCI MASS: 270 (M+H)$^+$

NMR (DMSO-d$_6$, δ): 0.89 (3H, t, J=7.2 Hz), 1.2–1.6 (4H, m), 3.74 (2H, s), 3.8–4.0 (2H, m), 8.25 (1H, s), 9.31 (4H, br s)

Elemental Analysis for C$_{11}$H$_{16}$ClN$_3$OS$_2$.0.75H$_2$O Calcd.: C, 41.37; H, 5.52; N, 13.16. Found.: C, 41.42; H, 5.40; N, 13.22.

The following compound was synthesized according to the similar manner to that of Example 1.

EXAMPLE 12

6-Amidino-2,3-dihydro-1-(2-methylthioethyl)-2-oxothieno[2,3-b][1,4]thiazine hydrochloride IR (KBr): 1664, 1594 cm$^{-1}$ NMR (DMSO-d$_6$, δ): 2.15 (3H, s), 2.71 (2H, t, J=7.4), 3.86 (2H, s), 4.13 (2H, t, J=7.4 Hz), 7.50 (1H, br s), 7.97 (1H, s), 8.15 (1H, br s), 9.13 (1H, br s)

EXAMPLE 13-1)

6-Ethoxycarbonyl-2-(1-ethoxy-1-iminomethyl)-4,5,6,7-tetrahydrobenzo[b]thiophene hydrochloride (1.51 g), 2.7 N ethanol solution of ammonia (1.41 ml) and EtOH (5 ml) was stirred at reflux for 4 hours. After evaporation, the resulting oil was purified by chromatography on silica gel (CHCl$_3$-MeOH as eluent), and subsequently washed with Et$_2$O to give 2-amidino-6-ethoxycarbonyl-4,5,6,7-tetrahydrobenzo[b]thiophene hydrochloride (1.20 g).

mp: 155–157° C.

IR (KBr): 3101 (br), 1726, 1660, 1573, 1513 cm$^{-1}$

APCI MASS: 253(M+H of free)

NMR (DMSO-d$_6$, δ): 1.20 (3H, t, J=7.1 Hz), 1.8 (1H, m), 2.1 (1H, m), 2.67 (2H, t, J=5.8 Hz), 2.8–3.2 (3H, m), 4.11 (2H, q, J=7.1 Hz), 7.81 (1H, s), 9.02 and 9.22 (4H, both br s)

EXAMPLE 13-2)

A mixture of 2-amidino-6-ethoxycarbonyl-4,5,6,7-tetrahydrobenzo[b]thiophene hydrochloride (1.15 g), and 6 N HCl (10 ml) was stirred at 70° C. for 9 hours. The resulting precipitate was washed with Et$_2$O to give 2-amidino-6-carboxy-4,5,6,7-tetrahydrobenzo[b]thiophene hydrochloride (0.96 g).

mp: >250° C.

IR (KBr): 3342, 3122, 2879, 1700, 1664, 1573, 1515 cm$^{-1}$

APCI MASS: 225 (M+H of free)

NMR (DMSO-d$_6$, δ): 1.83 (1H, m), 2.10 (1H, m), 2.6–3.2 (5H, m), 7.82 (1H, s), 9.06 and 9.24 (4H, both br s)

EXAMPLE 13-3)

To a mixture of 2-amidino-6-carboxy-4,5,6,7-tetrahydrobenzo[b]thiophene hydrochloride (0.91 g), water (20 ml), and dioxane (40 ml) was dropwise added di-tert-butyl dicarbonate (0.88 ml) maintaining to pH 9.5–10, and was stirred at r.t. for 2 hours. The reaction mixture was adjusted to pH 4 with 6 N HCl, and was extracted with AcOEt. The separated organic layer was washed with water, and dried over MgSO$_4$, and evaporated. The resulting precipitate was washed with n-hexane to give 2-(N$^1$-tert-butoxycarbonylamidino)-6-carboxy-4,5,6,7-tetrahydrobenzo[b]thiophene (0.86 g).

NMR (DMSO-d$_6$, δ): 1.42 (9H, s), 1.83 l(1H, m), 2.10 (1H, m), 2.6–3.2 (5H, m), 7.66 (1H, s), 8.91 (3H, br s)

EXAMPLE 13-4)

To a mixture of 2-(N$^1$-tert-butoxycarbonylamidino)-6-carboxy-4,5,6,7-tetrahydrobenzo[b]thiophene (0.40 g), CH$_2$Cl$_2$ (10 m), and dimethylformamide (DMF) (2 ml) was added triethylamine (0.17 ml) at r.t., and then O-benzotriazol-1-yl-N,N,N',N'-tetramethyluronium hexafluorophosphate (0.40 g) was added thereto. The reaction mixture was stirred at r.t. for 15 minutes. To the reaction mixture were added N,O-dimethylhydroxyamine hydrochloride (0.13 g) and triethylamine (0.19 ml), and the mixture was stirred at r.t. for 1 hour. After removal of solvents by nitrogen flow, the reaction mixture was added into a mixture of AcOEt and water. The separated organic layer was washed with water, and brine, and dried over MgSO$_4$. After evaporation of the filtrate, the resulting precipitate was washed with isopropyl ether to give 2-(N$^1$-tert-butoxycarbonylamidino)-6-(N-methyl-N-methoxycarbamoyl)-4,5,6,7-tetrahydrobenzo[b]thiophene which was used in the following reaction without further purification.

EXAMPLE 13-5)

A mixture of crude 2-(N$^1$-tert-butoxycarbonylamidino)-6-(N-methyl-N-methoxycarbamoyl)-4,5,6,7-tetrahydrobenzo[b]thiophene (0.05 g), water (0.06 ml), and trifluoroacetic acid (TFA) (0.6 ml) was stirred at r.t. for 2 hours. After removal of solvent by nitrogen flow, the resulting precipitate was washed with Et$_2$O to give 2-amidino-6-(N-methyl-N-methoxycarbamoyl)-4,5,6,7-tetrahydrobenzo[b]thiophene trifluoroacetate (40.2 mg).

IR (KBr): 3301, 3085, 1670, 1577, 1515 cm$^{-1}$

APCI MASS: 268 (M+H of free)

NMR (DMSO-d$_6$, δ): 1.83 (1H, m), 2.10 (1H, m), 2.6–3.2 (5H, m), 3.15 (3H, s), 3.71 (3H, s), 7.84 (1H, s), 8.89 and 9.11 (4H, both br s)

EXAMPLE 13-6)

To a mixture of 2-(N$^1$-tert-butoxycarbonylamidino)-6-(N-methyl-N-methoxycarbamoyl)-4,5,6,7-tetrahydrobenzo[b]thiophene (0.37 g), Et$_2$O (10 ml), and tetrahydrofuran (THF) (2 ml) was added lithium aluminum hydride (76.4 mg) at 0° C. under nitrogen atmosphere. The reaction mixture was stirred under the same conditions for 30 minutes. To the reaction mixture was added a saturated aqueous solution of ammonium hydrochloride to quench the reaction. The reaction mixture was added into a mixture of AcOEt and water. After removal of resulting insoluble precipitates by filtration, the separated organic layer was washed with water, and brine, and dried over MgSO$_4$. After evaporation of the filtrate, the resulting precipitate was washed with isopropyl ether to give 2-(N$^1$-tert-butoxycarbonylamidino)-6-formyl-4,5,6,7-tetrahydrobenzo[b]thiophene (0.26 g), which was used in the following next reaction without further purification.

The following compound was obtained according to a similar manner to that of Example 13-5).

EXAMPLE 13-7)

2-Amidino-6-formyl-4,5,6,7-tetrahydrobenzo[b]thiophene trifluoroacetate mp: 191–194° C.
IR (KBr): 3083, 1672, 1579, 1517 cm$^{-1}$
MASS (z/e): 209 (M+H)$^+$ of free
NMR (DMSO-d$_6$, δ): 1.80 (1H, m), 2.10 (1H, m), 2.67 (2H, t, J=6.2 Hz), 2.6–3.2 (3H, m), 7.73 (1H, s), 8.95 and 9.11 (4H, both br s), 9.71 (1H, s)

EXAMPLE 14-1)

The following compound was obtained according to a similar manner to that of Example 3.

6-Amidino-2,3-dihydro-1-(ethoxycarbonylacetyl)thieno[2,3-b][1,4]thiazine hydrochloride (+) APCI MASS: 314 (M+H)$^+$
NMR (DMSO-d$_6$, δ): 1.1–1.3 (3H, m), 3.3–3.5 (2H, m), 3.83 (2H, s), 3.9–4.2 (4H, m), 8.51 (1H, s), 9.17 (4H, s)

EXAMPLE 14-2)

The following compound was obtained according to a similar manner to that of Example 9–2).

6-Amidino-1-carboxyacetyl-2,3-dihydrothieno[2,3-b][1,4]thiazine hydrochloride

IR (Nujol): 1700, 1655, 1625 cm$^{-1}$
NMR (DMSO-d$_6$, δ): 3.0–3.2 (2H, m), 3.25 (2H, s), 3.4–3.6 (2H, m), 7.51 (1H, s), 8.97 and 9.14 (4H, each s)

EXAMPLE 15

The following compound was obtained according to a similar manner to that of Example 3.

6-Amidino-1-benzoyl-2,3-dihydrothieno[2,3-b][1,4]thiazine hydrochoride (+) APCI MASS: 304 (M+H)$^+$
NMR (DMSO-d$_6$, δ): 3.3–3.5 (2H, m), 3.9–4.1 (2H, m), 7.53 (5H, s), 8.29 (1H, s), 9.19 (4H, s)

EXAMPLE 16

The following compound was obtained according to a similar manner to that of Example 3.

1-Acetyl-6-amidino-2,3-dihydrothieno[2,3-b][1,4]thiazine hydrochloride (+) APCI MASS: 242 (M+H)$^+$
NMR (DMSO-d$_6$, δ): 2.25 (3H, s), 3.3–3.4 (2H, m), 3.9–4.1 (2H, m), 8.44 (1H, s), 9.24 (4H, br s)

EXAMPLE 17-1)

The following compound was obtained according to a similar manner to that of Example 1, which was used in the next reaction without further purification.

6-Amidino-2,3-dihydro-1-ethylthieno[2,3-b][1,4]thiazine hydrochloride

EXAMPLE 17-2)

The following compound was obtained according to a similar manner to that of Example 13–3).

6-(N$^1$-tert-Butoxycarbonylamidino)-2,3-dihydro-1-ethylthieno[2,3-b][1,4]thiazine (+) APCI MASS: 328 (M+H)$^+$
NMR (DMSO-d$_6$, δ): 1.06 (3H, t, J=7.0 Hz), 1.42 (9H, s), 3.0–3.2 (2H, m), 3.25 (2H, q, J=7.0 Hz), 3.4–3.5 (2H, m), 7.73 (1H, s), 8.87 (2H, br s)

EXAMPLE 17-3)

A solution of 6-(N$^1$-tert-butoxycarbonylamidino)-2,3-dihydro-1-ethylthieno[2,3-b][1,4]thiazine (0.51 g) in trifluoroacetic acid (4.5 ml) and water (0.5 ml) was stirred for 72 hours at room temperature. The solvent was evaporated in vacuo and the residue was pulverized from diethyl ether to give 6-amidino-2,3-dihydro-1-ethylthieno[[2,3-b][1,4]thiazine trifluoroacetate (0.50 g).

(+) APCI MASS: 228 (M+H)$^+$
NMR (DMSO-d$_6$, δ): 1.0–1.2 (3H, m), 3.1–3.6 (6H, m), 7.74 (1H, s), 9.02 (4H, br s)

What is claimed is:

1. A compound of the formula:

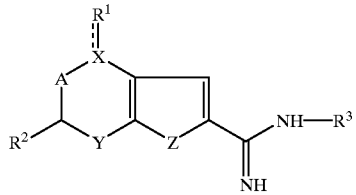

(I)

in which

R$^1$ is hydrogen, optionally substituted lower alkylcarbamoyl(lower)alkylidene, lower alkylidene, lower alkyl, optionally substituted ar(lower)alkyl, cyclo(lower)alkyl(lower)alkyl, protected carboxy(lower)alkyl, carboxy(lower)alkyl, hydroxy(lower)alkyl, optionally substituted lower alkylcarbamoyl(lower)alkyl, lower alkylthio(lower)alkyl, carboxy(lower)alkanoyl, protected carboxy(lower)alkanoyl, aroyl, lower alkanoyl, or optionally substituted arylcarbamoyl(lower)alkyl, R$^2$ is hydrogen, carboxy, protected carboxy, formyl or N-(lower)alkyl-N-(lower)alkoxycarbamoyl, R$^3$ is hydrogen or amidino-protective group, A is lower alkylene or carbonyl, X is

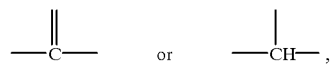

Y is lower alkylene,

Z is —S— or —O—, and the line: ═ is a single bond or a double bond, or pharmaceutically acceptable salts thereof.

2. The compound of claim 1, wherein

R$^1$ is hydrogen; lower alkylcarbamoyl(lower)alkylidene optionally substituted by halogen; lower alkylidene; lower alkyl; ar(lower)alkyl optionally substituted by the group consisting of lower alkyl, lower alkoxy and lower alkylenedioxy; cyclo(lower)alkyl(lower)alkyl; lower alkoxycarbonyl(lower)alkyl; carboxy(lower)alkyl; hydroxy(lower)alkyl; lower alkylcarbamoyl (lower)alkyl optionally substituted by halogen; lower alkylthio(lower)alkyl; carboxy(lower)alkanoyl; lower alkoxycarbonyl(lower)alkanoyl; aroyl; lower alkanoyl; or arylcarbamoyl(lower)alkyl optionally substituted by the group consisting of lower alkyl, lower alkoxy and lower alkylenedioxy;

$R^2$ is hydrogen, carboxy, lower alkoxycarbonyl, formyl, or N-(lower)alkyl-N-(lower)alkoxycarbamoyl, and $R^3$ is hydrogen or lower alkoxycarbonyl.

3. The compound of claim 1, wherein

X is

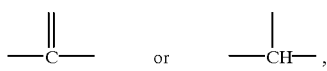

and

Y is lower alkylene.

4. A process for the preparation of a compound of the formula:

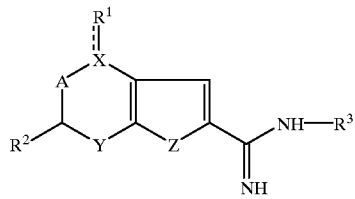

(I)

in which $R^1$, $R^2$, $R^3$, A, X, Y, Z and the line: ═ are each as defined in claim 1, or salts thereof, which comprises (a) reducing a compound of the formula:

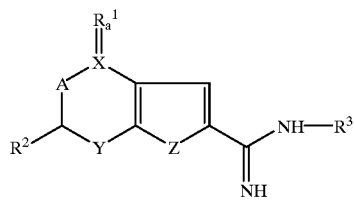

(I-b)

or a salt thereof to give a compound of the formula:

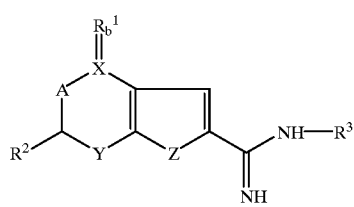

(I-c)

or a salt thereof; or (b) reacting a compound of the formula:

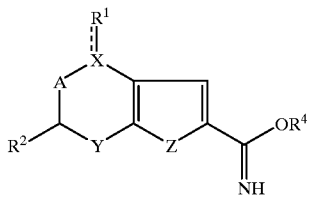

(III)

or a salt thereof with ammonia or a salt thereof to give a compound of the formula (I-a), or a salt thereof; or (c) subjecting a compound of the formula:

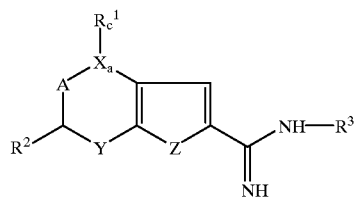

(I-d)

or a salt thereof to a removal reaction of the carboxy-protective group in $R_c^1$ to give a compound of the formula:

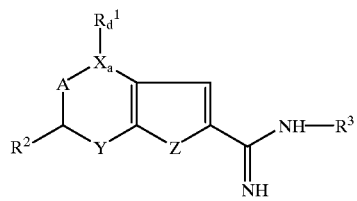

(I-e)

or a salt thereof; or (d) subjecting a compound of the formula:

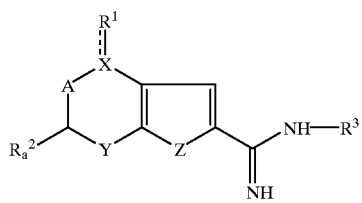

(I-f)

or a salt thereof to a removal of the carboxy-protective group in $R_a^2$ to give a compound of the formula:

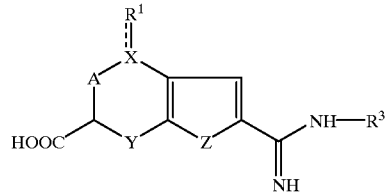

(I-g)

or a salt thereof (e) introducing an amidino-protective group into a compound of the formula:

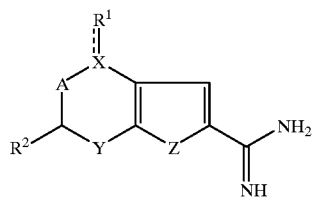
(I-a)

or a salt thereof, to give a compound of the formula:

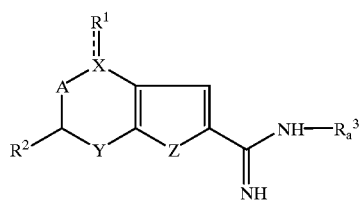
(I-h)

or a salt thereof; or (f) reacting a compound of the formula:

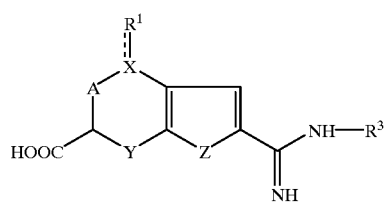
(I-g)

or its reactive derivative at the carboxy group, or a salt thereof, with N-(lower)alkyl-N-(lower)alkoxyamine or a salt thereof, to give a compound of the formula:

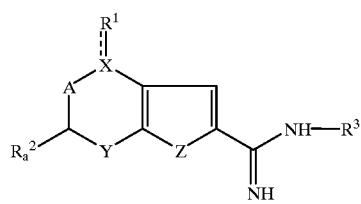
(I-i)

or a salt thereof; or (g) subjecting a compound of the formula:

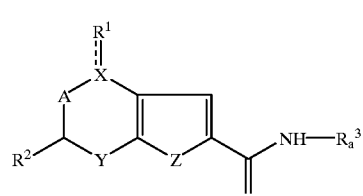
(I-h)

or a salt thereof; or to a removal reaction of the amidino-protective group of $R_a^3$, to give a compound of the formula (I-a) or a salt thereof; or (h) reducing a compound of the formula:

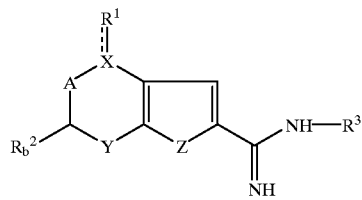
(I-j)

or a salt thereof, to give a compound of the formula

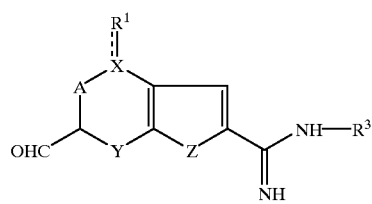
(I-k)

or a salt thereof;

in which $R^1, R^2, R^3, A, X, Y, Z$ and the line: ═ are each as defined above, $R_a^1$ is optionally substituted lower alkylcarbamoyl(lower)alkylidene or lower alkylidene, $R_b^1$ is optionally substituted lower alkylcarbamoyl(lower)alkyl or lower alkyl, $R_c^1$ is protected carboxy(lower)alkyl, $R_d^1$ is carboxy(lower)alkyl, $R^{a2}$ is protected carboxy, $R_b^2$ is N-(lower)alkyl-N-(lower)alkoxycarbamoyl, $R_a^3$ is amidino-protective group, $R^4$ is ester residue, $X_a$ is

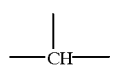

5. A pharmaceutical composition which comprises, as an active ingredient, a compound of claim 1 or a pharmaceutically acceptable salt thereof in admixture with pharmaceutically acceptable carriers or excipients.

6. A method for treatment of diseases initiated by urokinase which comprises administering an effective amount of a compound of claim 1 or a pharmaceutically acceptable salt thereof to a human being or an animal.

* * * * *